Figure 11:
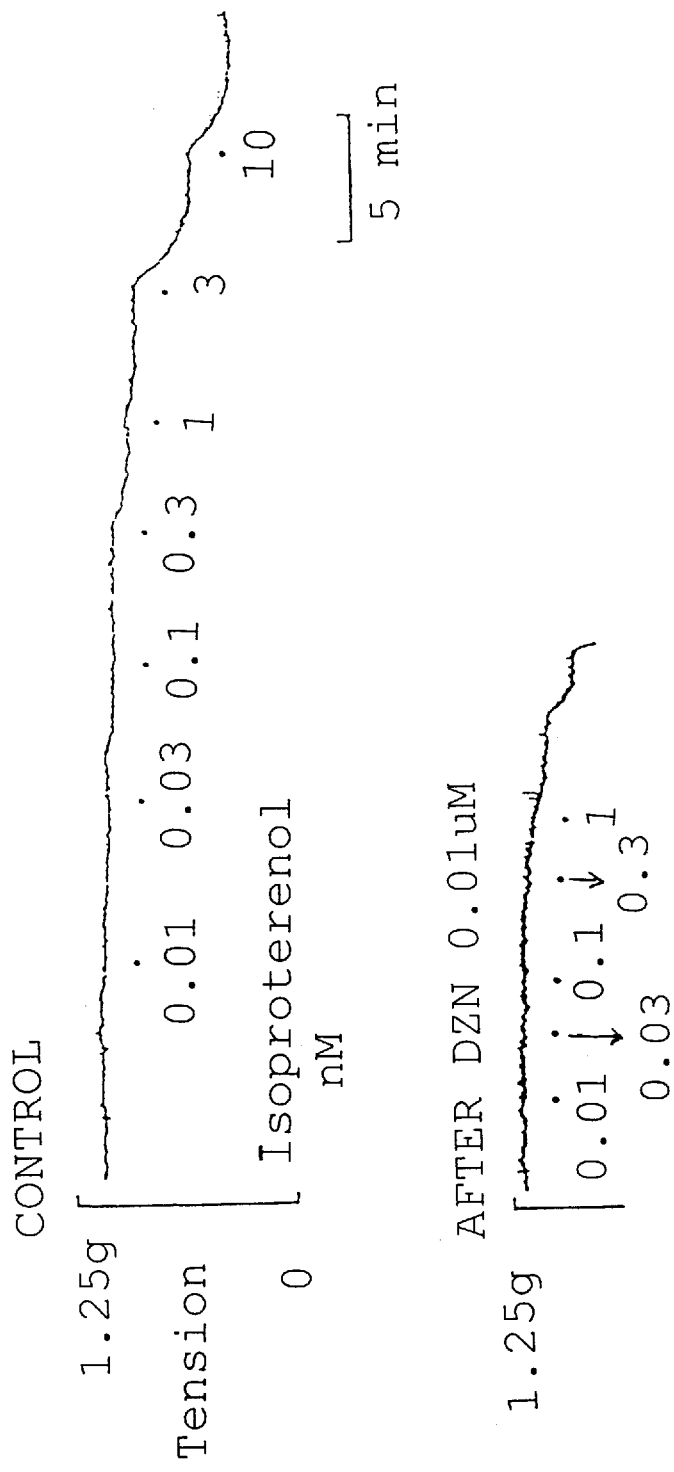

United States Patent [19]

Chen

[11] Patent Number: 5,804,603
[45] Date of Patent: Sep. 8, 1998

[54] SYNTHESIZED β-ADRENERGIC BLOCKERS DERIVATIVES OF GUAIACOL

[75] Inventor: Ing-Jun Chen, Kaohsiung, Taiwan

[73] Assignee: National Science Council, Taipei, Taiwan

[21] Appl. No.: 559,208

[22] Filed: Nov. 13, 1995

Related U.S. Application Data

[63] Continuation-in-part of Ser. No. 157,473, Nov. 26, 1993, abandoned.

[51] Int. Cl.$^6$ ........................ A61K 31/165; C07C 233/05
[52] U.S. Cl. ............................................. 514/630; 564/219
[58] Field of Search ..................................... 568/652, 654, 568/308; 564/219; 514/630

[56] References Cited

U.S. PATENT DOCUMENTS 3,663,607   5/1972   Barrett et al. ........................ 260/501.1

*Primary Examiner*—José G. Dees
*Assistant Examiner*—Mary C. Cebulak
*Attorney, Agent, or Firm*—Bucknam and Archer

[57] ABSTRACT

Compounds of formula I

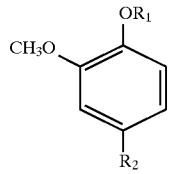

in which $OR^1$ is $-OR_3NR_4$, in which R3 is a secondary alcohol group with 1.0 to 6 carbon atoms; a cyclic oxygen containing group with two carbon atoms; a pyridylmethyl or a piperidyl-ethyl group, $R_2$ is alkyl, an ester group, an aldehyde group, a carboxylic acid group or a ketone group with 3 to 6 carbon $-O-CONHR_9$ atoms, the group $O-R_7NCOR_8$ or the group $-O-CONHR_9$ in which $R_4$ is an alkyl group with 1 to 8 carbon atoms, $R_7$ is an alkylene group with 1 to 6 carbon atoms, each of $R_8$ and R9 is an alkyl group with 1 to 12 carbon atoms and their pharmaceutically acceptable acid addition salts, are selective β-blockers, antagonists of platelet aggregation, and β-receptor binding. The processes of preparation, compositions, method of treatment are also described.

3 Claims, 22 Drawing Sheets

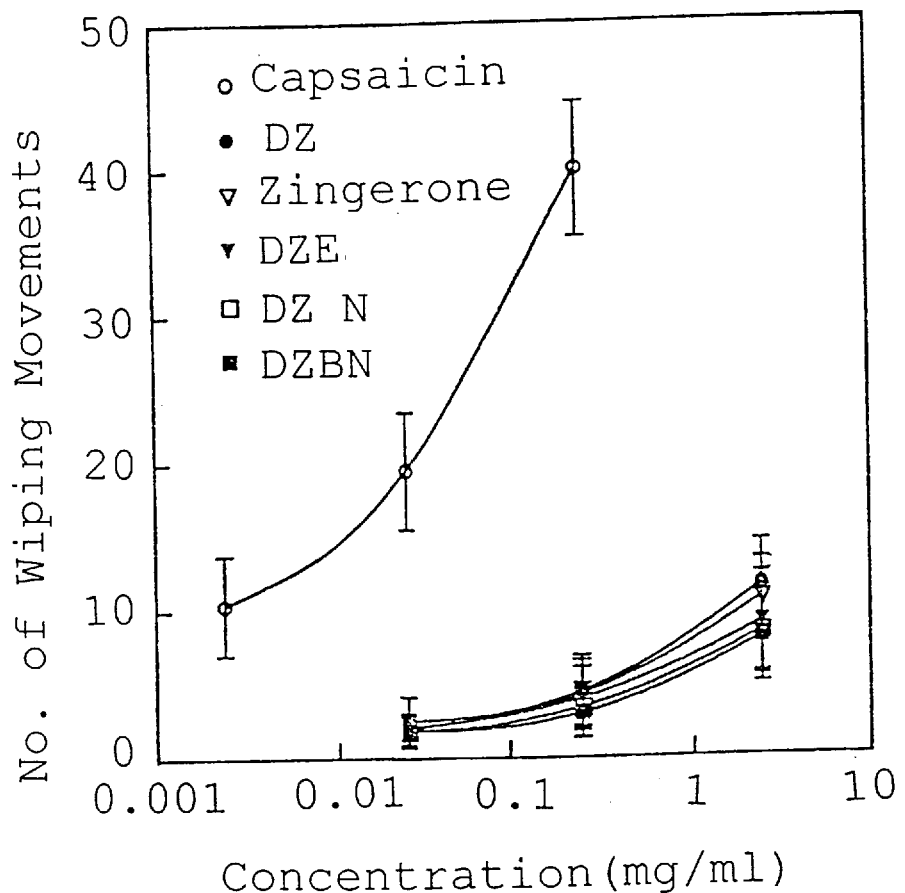
FIG. 1 Comparison Concentration-Wiping Response Curves of various, Compounds, Wiping response indicates the extent of irritation

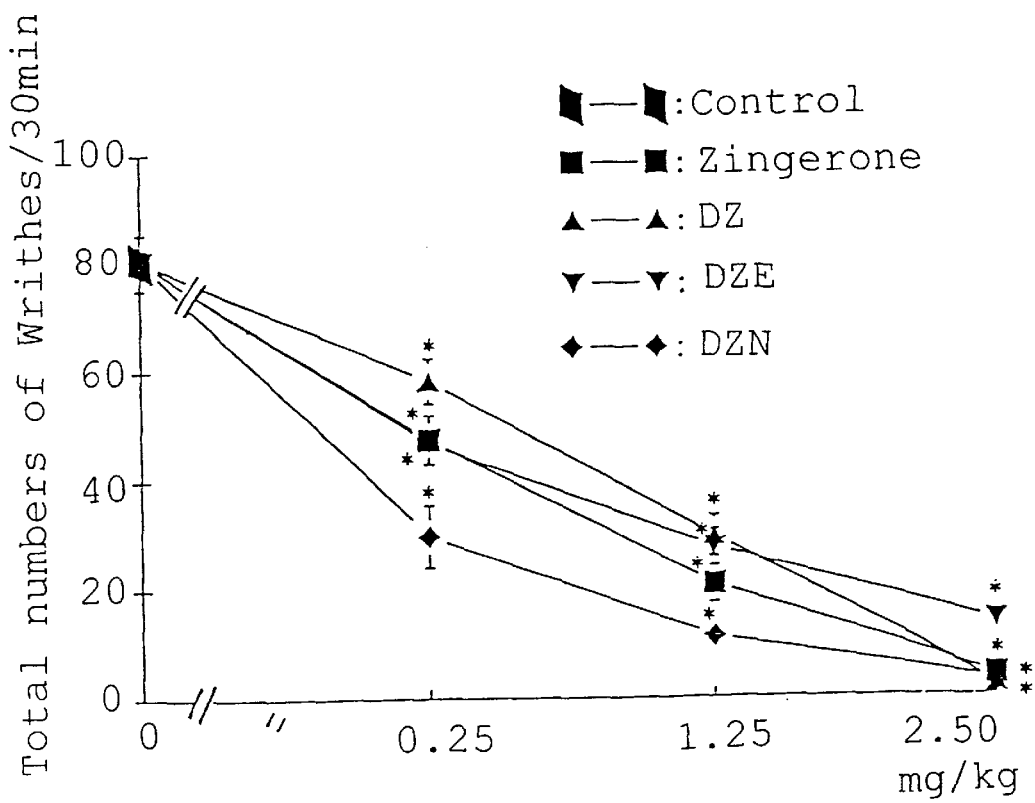
FIG. 2 Dose-response curves of zingerone, dehydrozingerone(DZ), DZE on responses to intraperitoneal injection of acetic acid in mice. Each point represents the mean ± S.E.M. (n=8), (* P< 0.05)

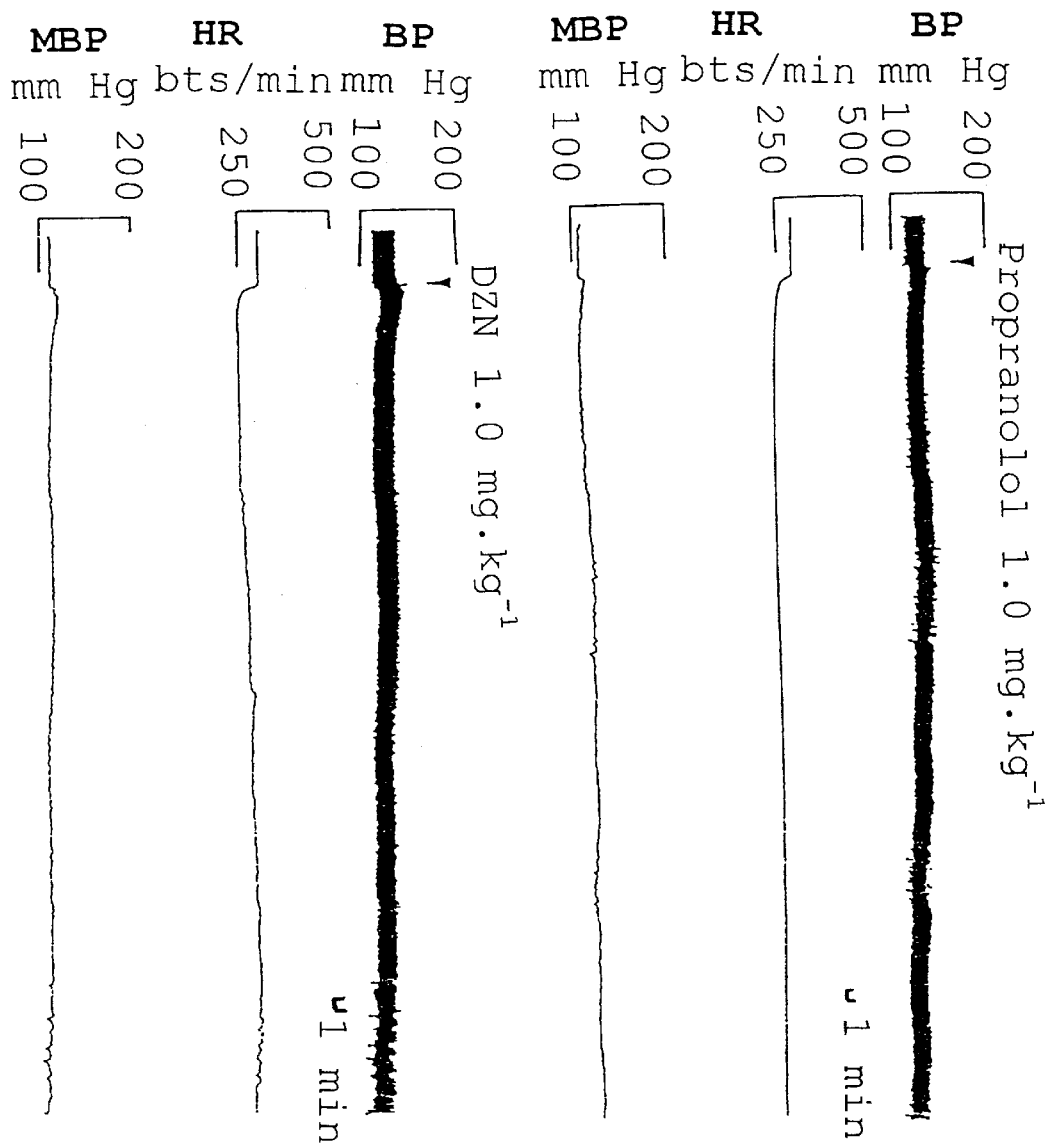
FIG.3 Effects of intravenous injection of propranolol and DZN on blood pressure heart rate in anesthetized rats.

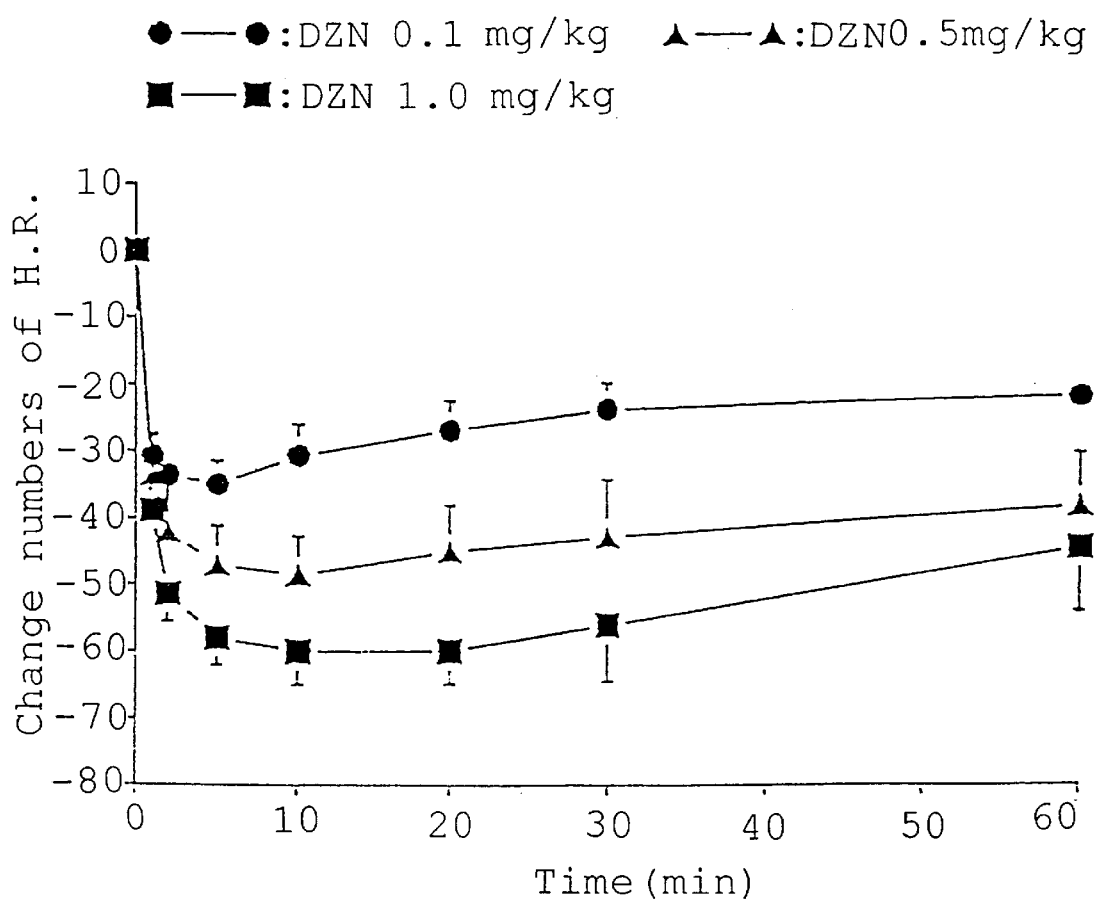
FIG. 4 Dose-dependent effects of DZN on heart rate in rats. Each point represents the mean ± SD. (n=8)

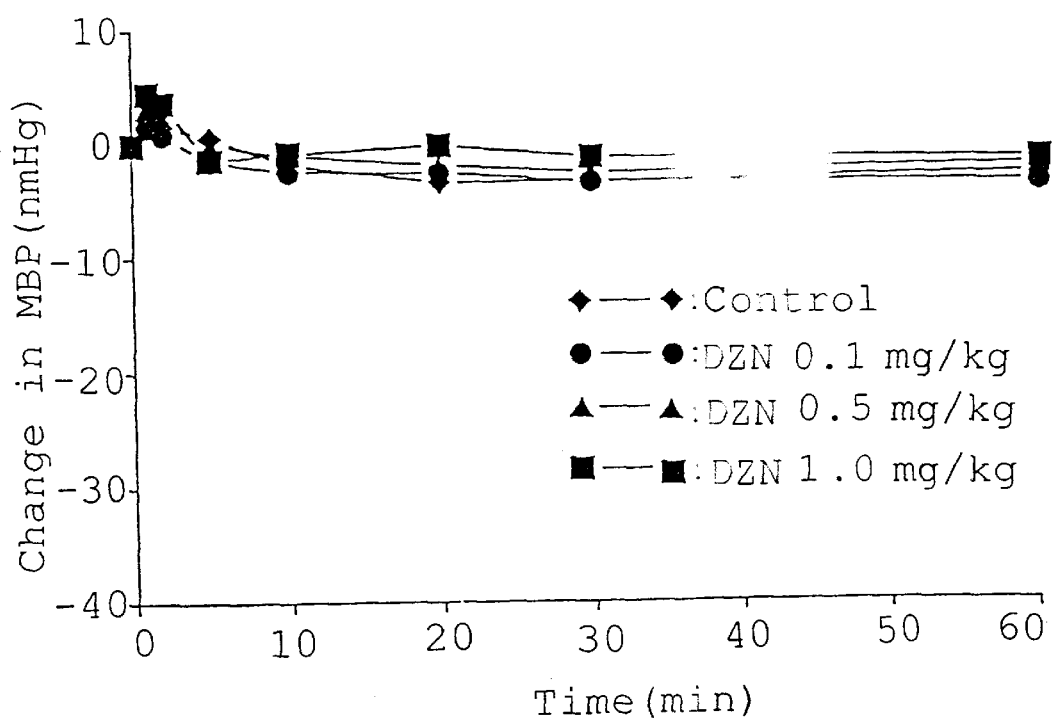
FIG. 5 Effects of DZN on mean blood pressure in rats.

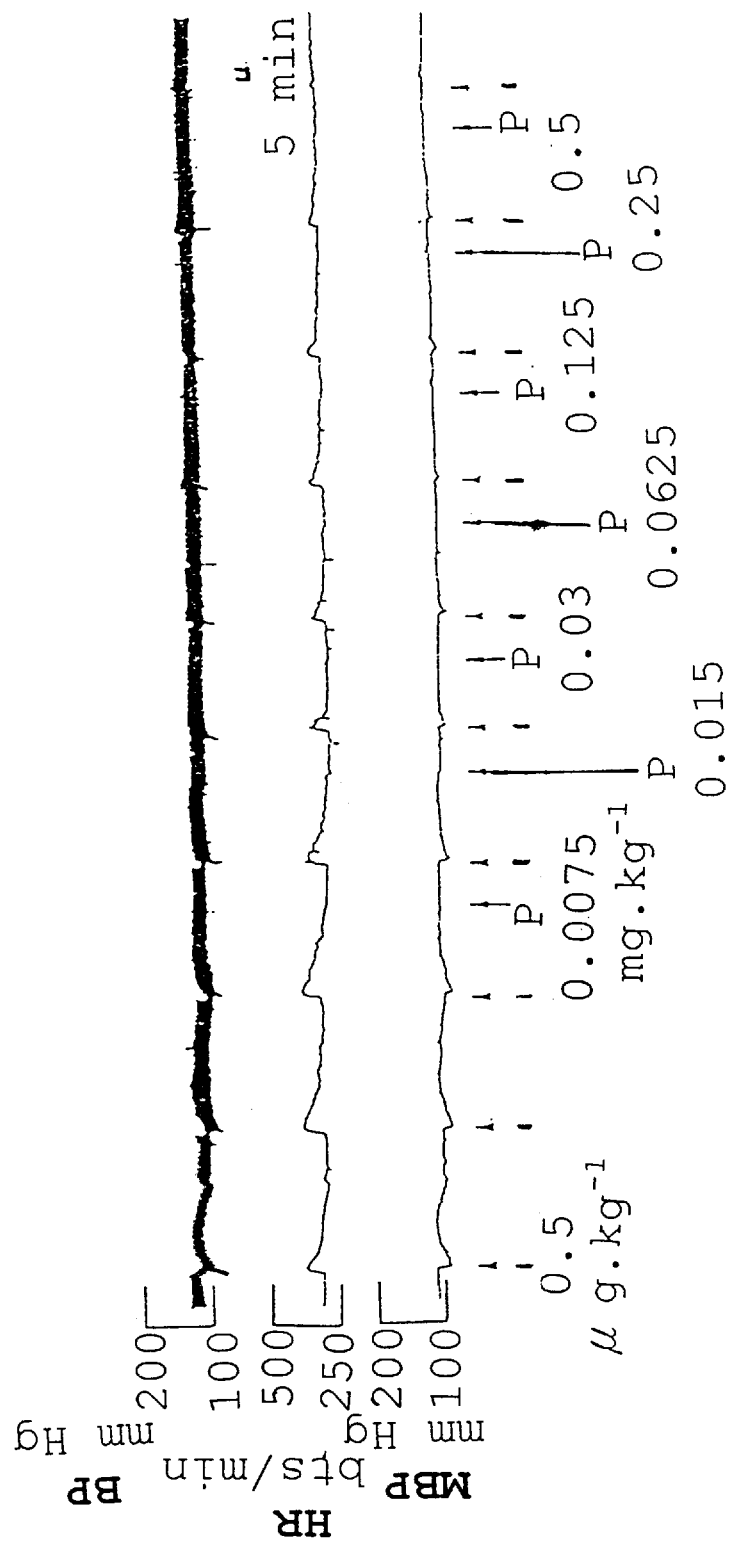
FIG. 6(A) Recording of blood pressure and heart rate of an anesthetized rat showing the effects of increasing dose of propranolol(P) and DZN(D) on the responses to 0.5 μg/kg isoproterenol(I).

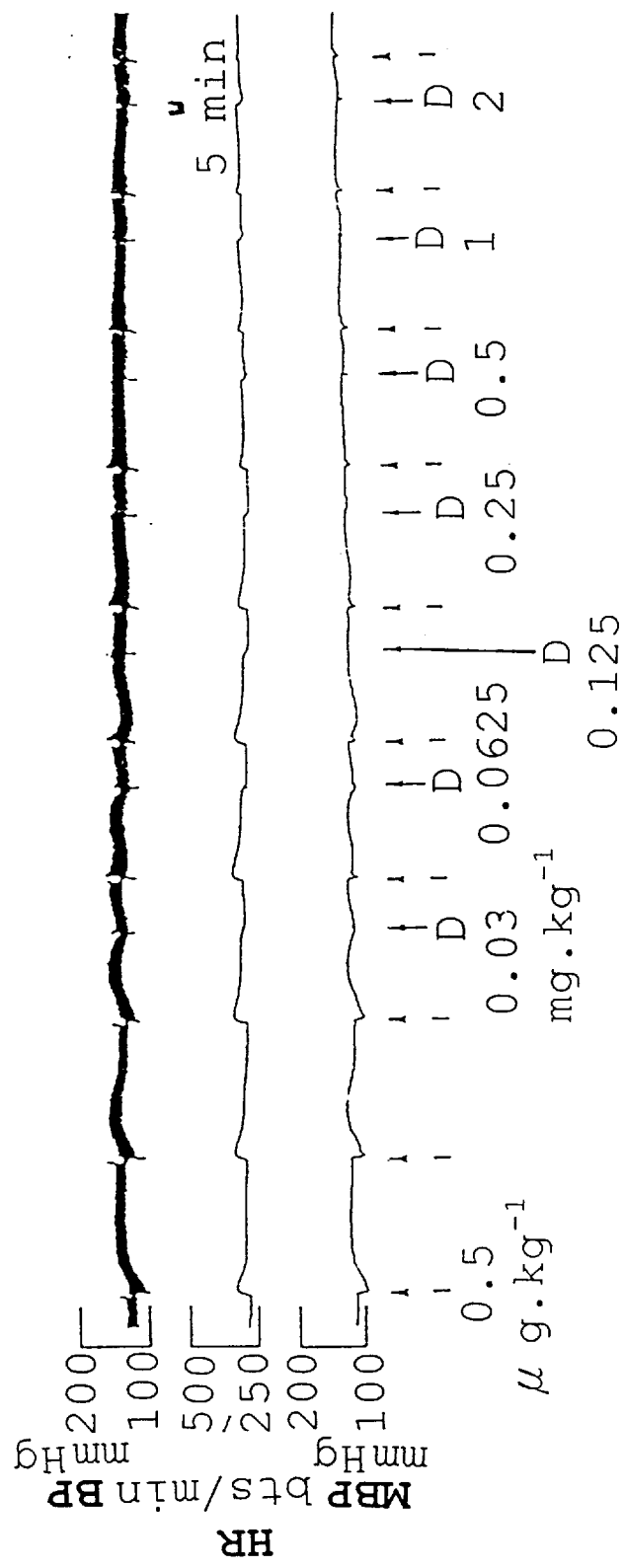
FIG. 6(B) Recording of blood pressure and heart rate of an anesthetized rat showing the effects of increasing dose of propranolol(P) and DZN(D) on the responses to 0.5 μg/kg isoproterenol(I).

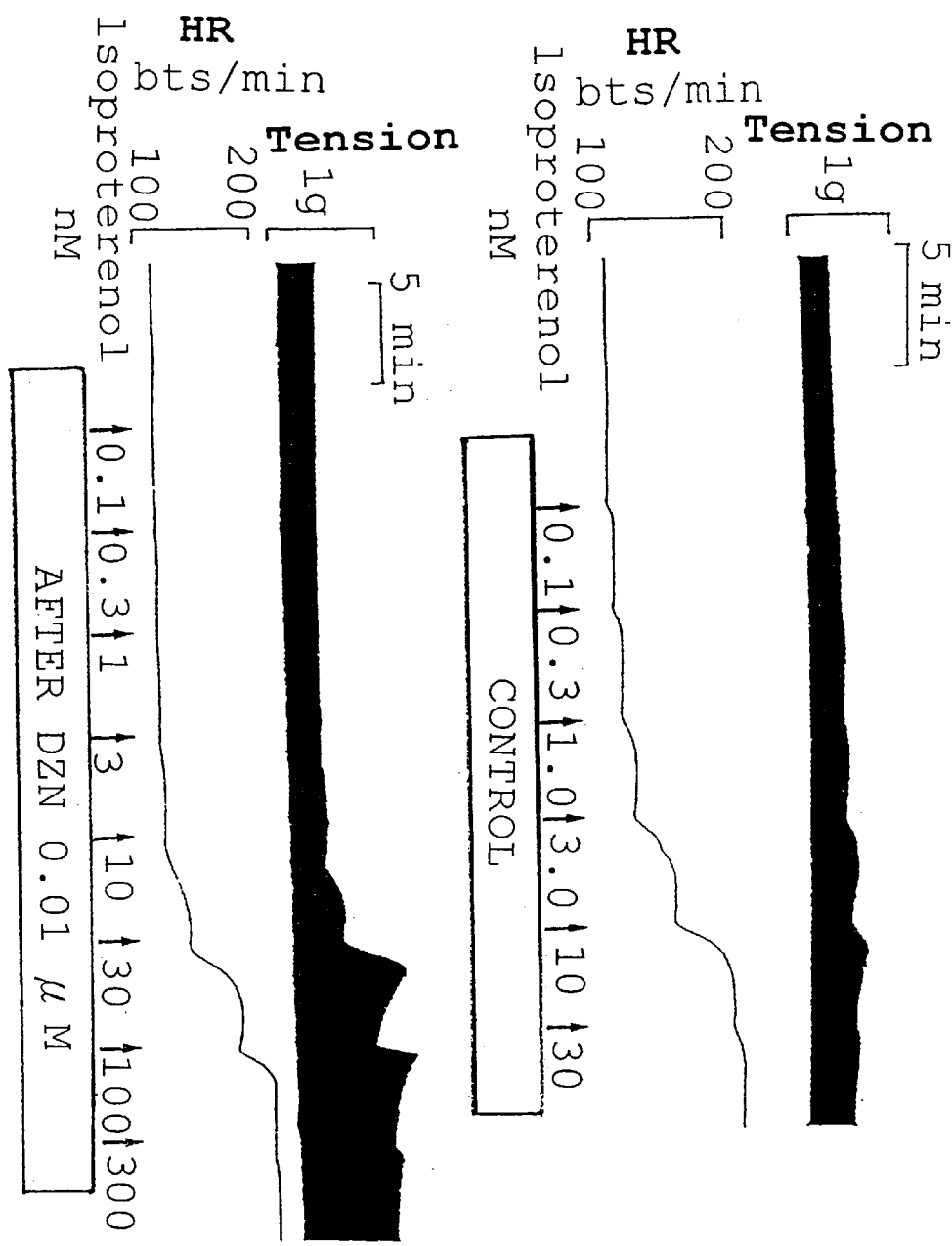
FIG. 7 Depression of maximal responses of tension and heart rate to isoproterenol by DZN.

FIG. 8 Depression of maximal responses of tension and heart rate to isoproterenol by DZN

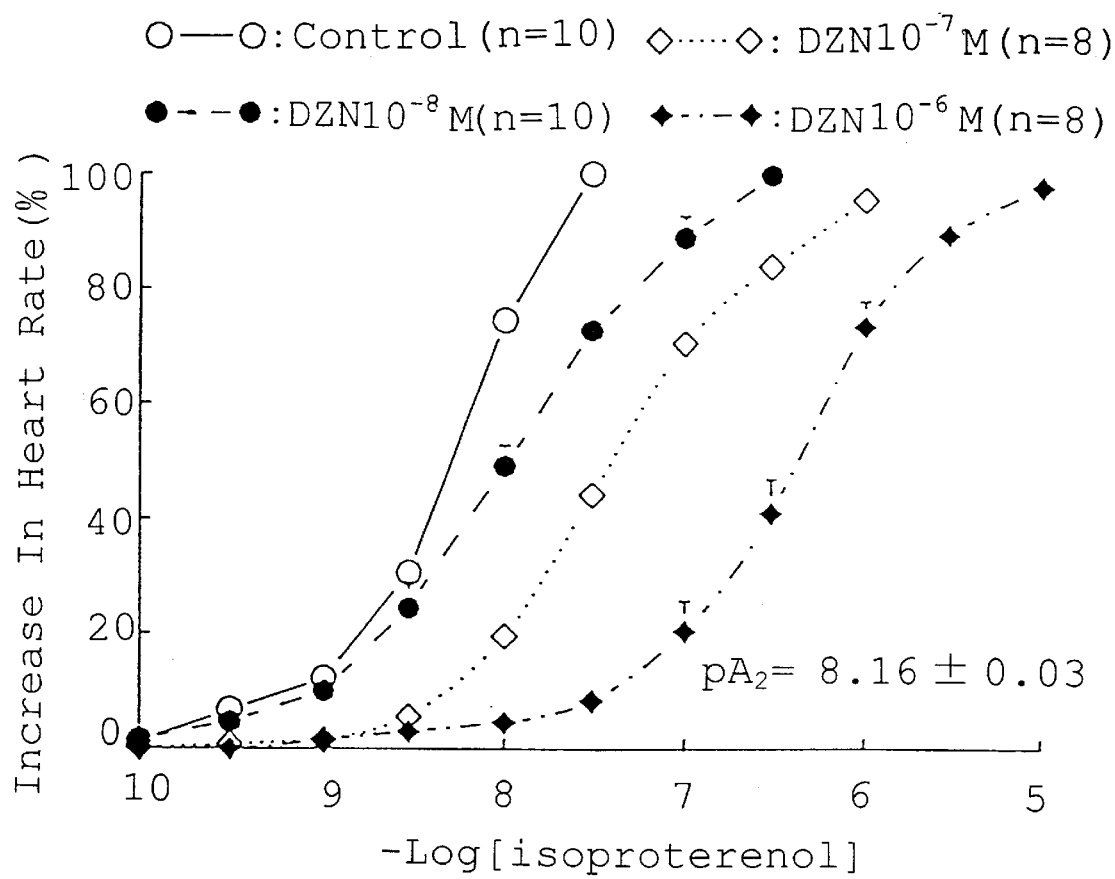
FIG. 9 Concentration effect curves on heart rate of isoproterenol alone or in the presence of DZN.

FIG. 10 Schedule plot for propranolol and DZN on guinea-pig isolated atrium using isoproterenol as agonist. Ordinate scale: logarithm of (concentration ratio$^{-1}$); abscissa scale: negative logarithm of molar concentration of propranolol and DZN.
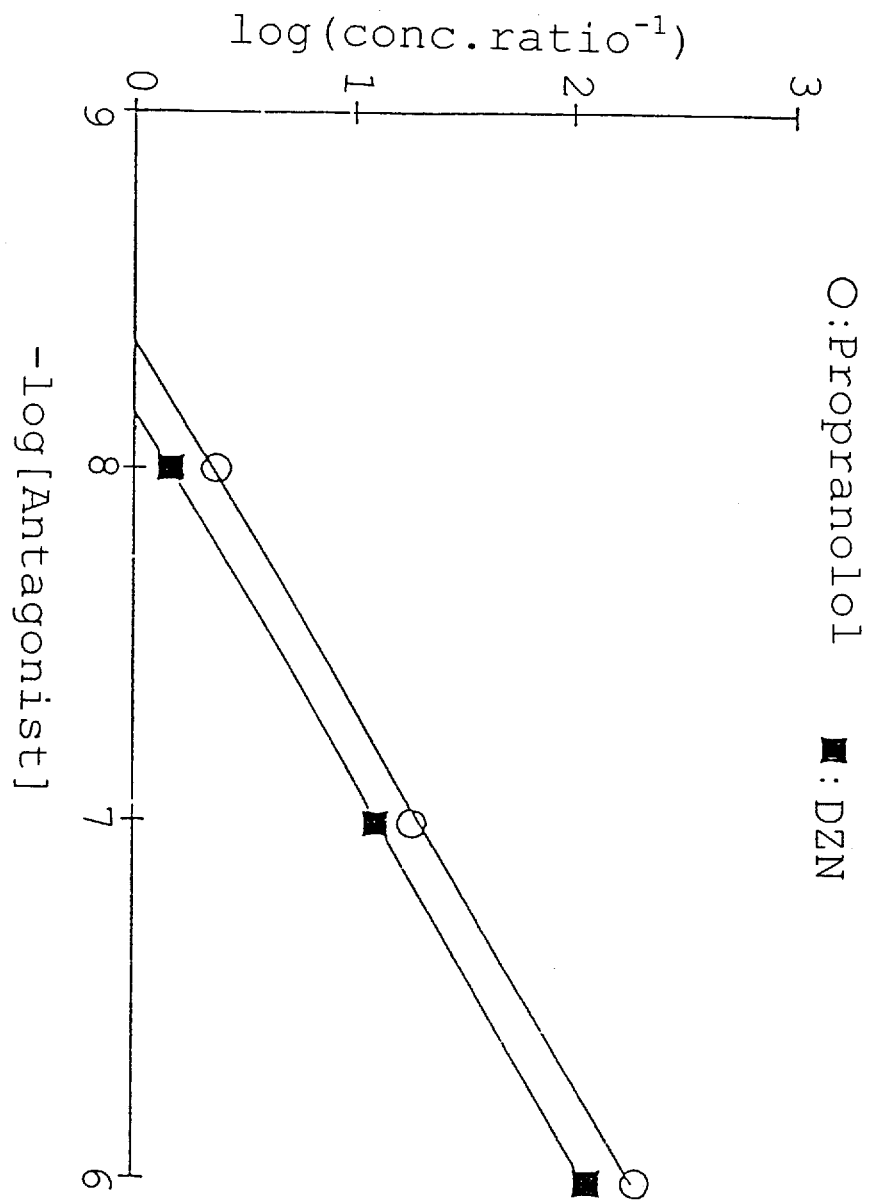

Inhibitory effects of maximal relaxant responses of tension to isoproterenol by DZM in isolated rat uterus horn strips.

Figure 12:
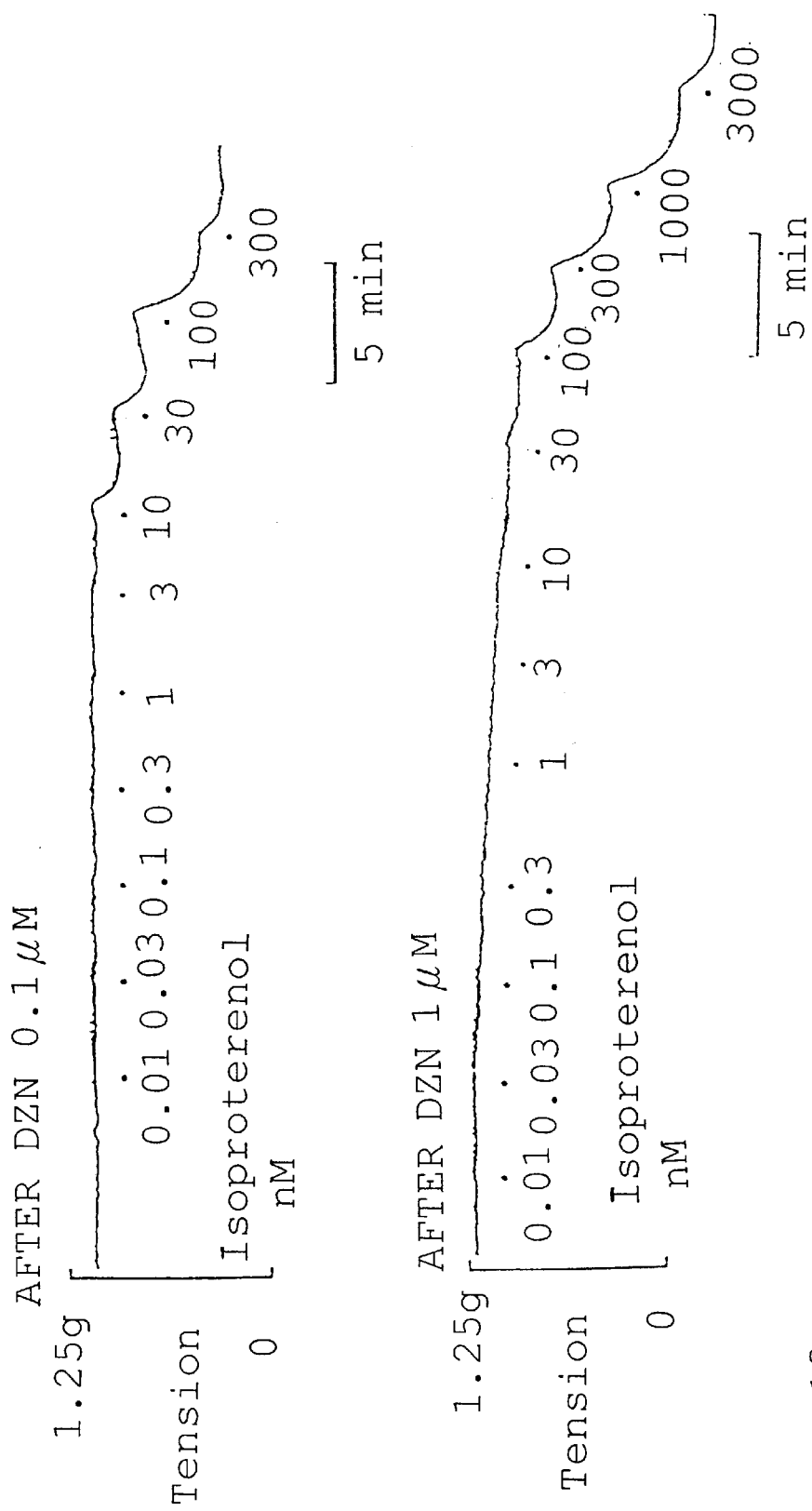

FIG. 12 Inhibitory effects of maximal relaxant responses of tension to isoproterenol by DZM in isolated rat uterus horn strips.

Concentration effect curves of the relaxing effect for isoproterenol alone or in the presence of DZN.

Figure 14:
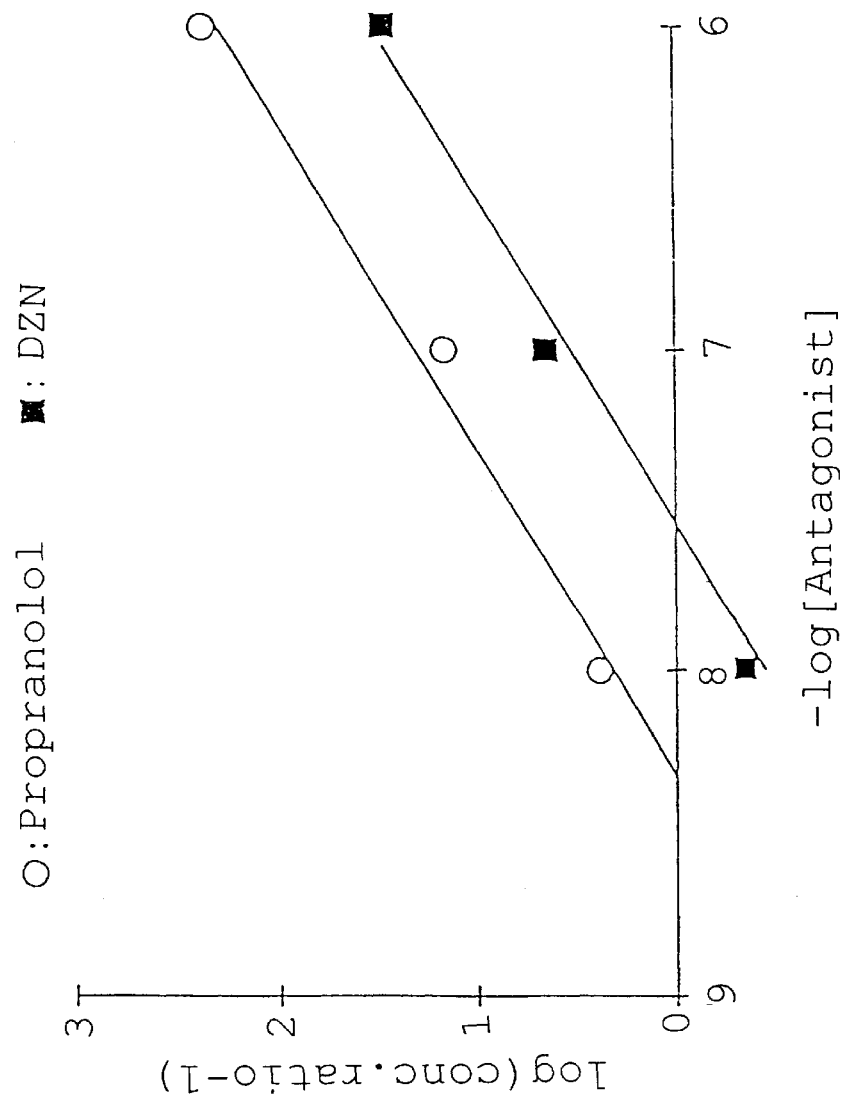

FIG.14 Schild plot for propranolol and DZN on rat isolated uterus horns using isoproterenol as agonist. Ordinate scale: logarithm of (concentration ratio-1); abscissa scale: negative logarithm of molar concentrations of propranolol and DZN.

Binding activity of various β-blockers on guinea-pig ventricular myocyte membrane binded with $^3$H-DHA Changes in tension and heart rate following the administration of various concentrations of isoproterenol, DZN and DZ to isolated atrium of reserpinized rats.

Positive chronotropic effects of various concentrations of isoproterenol, DZN and DZ on spontaneously beating atrium from reserpinized rats. Ordinate scale: positive chronotropic effect in % of maximal response, abscissa scale: negative logarithm of molar concentrations of Compounds.

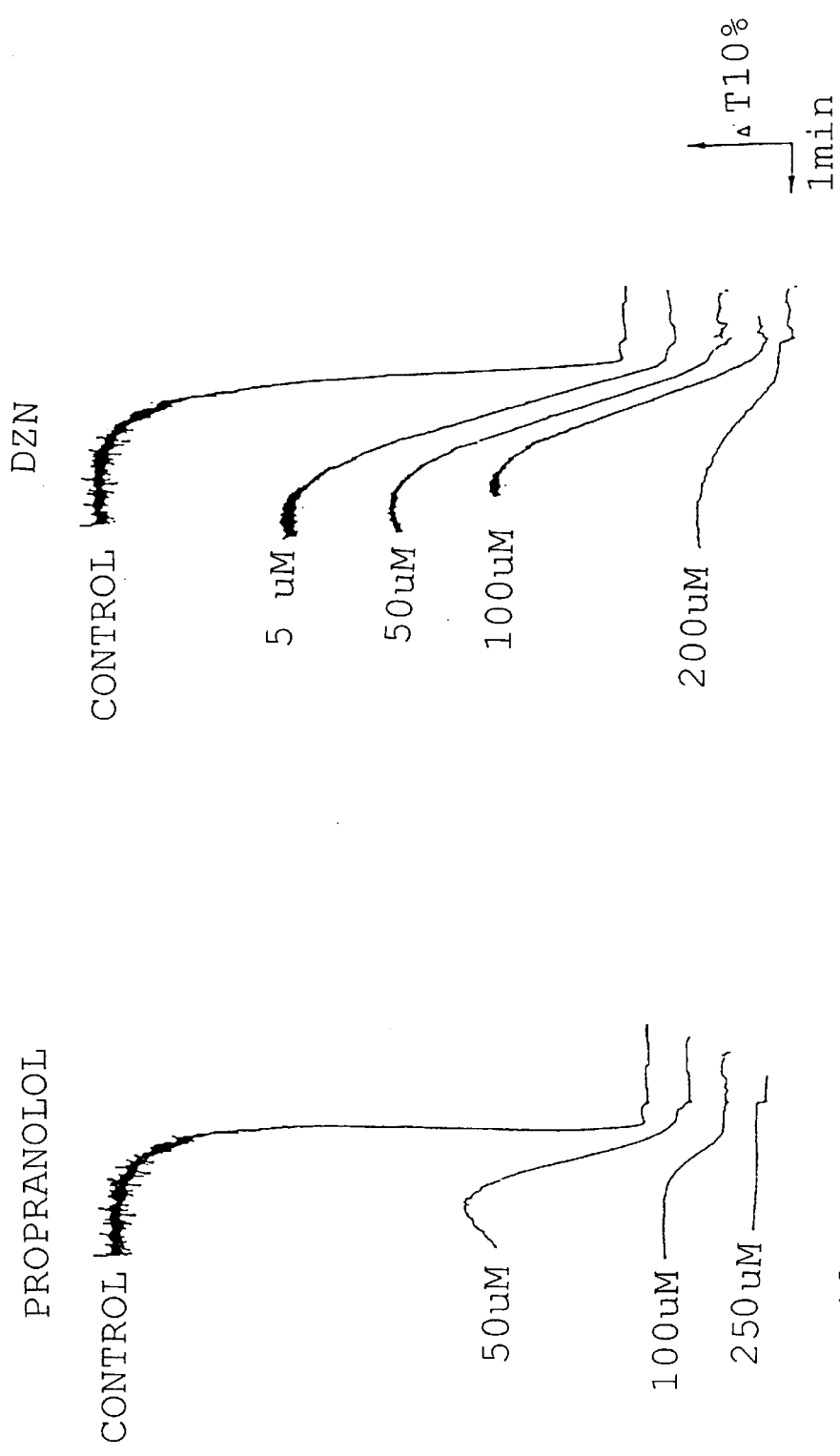
FIG. 18 Effects of propranolo and DZN on collagen-induced aggregation. Platelets were incubated with saline (control) or compound (final concentration indicated) and stirred for 30 sec, then collagen (10 μg/ml) was added to trigger the aggregation.

Effects of 1 (capsaicin, $10^{-7}$ M) and example 8 ($10^{-5}$ -$10^{-4}$ M ) on tension and contractile rate of apontaneously beating guinea pig right atrium.

Typical records of systemic blood
preasure(BP)and heart rate(HR)
following iv injection of example
8(1mg/kg)in anesthetized rats.

Effects of iv injection of 1(capsaicin), 2(nonivamide), at 3(example 7) on blood pressure and heart rate in normal rats. Vertical lines represent SE(n=8). Statistically significant differences compared with capsaicin using Student's t test is shown as *P<0.05 and **P<0.001.

SYNTHESIZED β-ADRENERGIC BLOCKERS DERIVATIVES OF GUAIACOL

This application is a Continuation-In-Part of U.S. Ser. No. 08/157,473 filed Nov. 26, 1993, abandoned.

FIELD OF THE INVENTION

This application relates to β-adrenergic blockers containing the guaiacol ring.

BACKGROUND OF THE INVENTION

Chinese crude drugs or spices eg. *Zingiber officinale, Eugenia caryophyllata, Allium sativum*, have been used in medicine and in flavoring foods. Crude ginger is used as an antiemetic and expectorant, an antitussive and accelerator of the digestive organs. Semidried old crude ginger is also used for stomachache, chest pain, low back pain, cough, common cold and as a cure for a form of edema being called "stagnate of water". Zingerone is the major component which accounts for the spicy character of ginger; gingerol and shogaol are other pungent components in ginger. Gingerol has cardio-tonic action, suppresses the contraction of isolated portal veins in mice, and modulates the eicosanoid-induced contraction of mouse and rat blood vessels. Shogaol exhibits pressor response. Both gingerol and shogaol are mutagenic, whereas zinger and zingerone have been found to exhibit antimutagenic activity. Shogaol has inhibitory activity on the carrageenin-induced paw edema and platelet aggregation.

It is known that drug-induced physiological responses are mediated through the binding of drugs to their specific receptors in various tissues and β-receptor blockade has been clinically used in cardio-vascular diseases. The pharmacological effects of β-blockers are evaluated based on (1) cardioselectivity, (2) α-adrenergic blocking action, (3) intrinsic sympathomimetic activity, (4) local anesthetic-activity, and (5) pharmacokinetic parameters related to the metabolism and distribution. Atenolol, Metoprolol, Acebutolol . . . etc. are clinically used as β-blockers and possess cardioselectivity. Some non-selective β-blockers are suitable for treating bronchial spasm and insulin-dependent diabetes. The selectivity of β-blockers is determined by comparing the dosage of each agent needed to produce inhibitory effects on $\beta_1$ and $\beta_2$ receptors in tissues. In addition to in vivo tests, cardiac tissue, adipose tissue, the smooth muscle of trachea, and uterus from animals or human lymphocyte are also used to examine the selectivity of β-blockers. It was reported first by Weksler, B. B. (1977), then by Greer, I. A. (1985) that β-blockers affect the platelet function.

Further, Srivastava, K. C. reported that lipid soluble β-blockers with membrane stabilizing activity inhibited the platelet coagulation and thromboxane synthesis. About the action mechanism of β-blockers on the platelet function, it has been suggested that β-blockers inhibit the activity of platelet phospholipase $A_2$ (Greer, I. A. et al, Thromb. Haemost., vol. 54, 480–84) or interfere with intracellular $Ca^{+2}$ mobilization (Weksler, B. B. et al, Blood, vol. 49, 185–96). β-blockers, such as Propanolol also inhibit platelet release and the adherence of platelets on collagen, but propanolol does not inhibit the shape change of platelets. The structure-activity relationship between many β-blockers and phenoxypropanolamine has been shown by Kierstead, R. W. et al (J. Med. Chem. vol. 26, 1561–69, 1983). They have also shown that replacement of the hydrogen atoms with isopropyl group in phenylethylamine produce better affinity with β-blockers.

SUMMARY OF THE INVENTION

An object of the present invention is to provide new guaiacoxy propanolamine derivatives of formula of, I, their related pharmaceutically acceptable salts and compositions comprising the same which are selective β-blockers, antagonists of platelet aggregation, and β-receptor binding

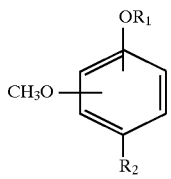

I in which $R_1$ is alkyl with 1 to 6 carbon atoms, hydrogen, the group $R_3NR_4$, or the group $R_5R_6$; in which $R_3$ is a secondary alcohol group with 1 to 6 carbon atoms, $R_2$ is an alkene, an ester, an aldehyde group, a carboxylic acid group or a ketone group with 3 to 6 carbon atoms, the group $R_7N$—$COR_8$, or the group —$CONHR_9$ in which $R_7$ is an alkyl group with 1 to 6 carbon atoms, $R_8$, $R_9$ are alkyl group with 1 to 12 carbon atoms $R_4$ is an alkyl group with 1 to 8 carbon atoms, $R_5$ is an alkyl group with 1 to 4 carbon atoms, $R_6$ is a cyclic oxygen containing group with 2 to 4 carbon atoms, provided that when $R_1$ is hydrogen, $R_2$ is a ketone group with 3–6 carbon atoms.

Another object of the invention is to provide β-adrenergic blockers compositions and a method of treatment of patients in need of treatment.

Another object of the invention is to provide processes for the preparation of the novel compounds and to pharmaceutical compositions comprising the same.

This invention has shown that even a minor chemical modification of the substituents on the aromatic ring of guaiacol-based compounds may result in a marked reduction of pain-producing potency and lead to a complete loss of antinociceptive activities, better) β-blockers activity, and less toxicity than that of natural pungent substances.

The reaction schemes are illustrated hereinbelow. The synthetic reactions are preferably carried out in the alkaline solution of starting materials like vanillin, and eugenol (formula V) illustrated only with respect to vanillin, and further reacted with compounds (formula II IV) to produce compound of formula I. According to the reaction scheme hereinbelow compound 2 (dehydrozingerone) was synthesized from vanillin of formula V, then the compound 2 was hydrogenated and converted to compound 1(zingerone). Treating compound 2 with the compound of formula II gave compound 3; amination of compound 3 with the compounds of formula IV in alcoholic solution produced the compound 4 or 6. The compound 5 was synthesized from compound 1 or hydrogenated from compound 4. $R_5$ is alkyl group with 1 to 4 carbon atoms, $R_6$ is a cyclic oxygen containing group with 2 to 4 carbon atoms and preferably the total number of carbon atoms of $R_5$ and $R_6$ is lower than six.

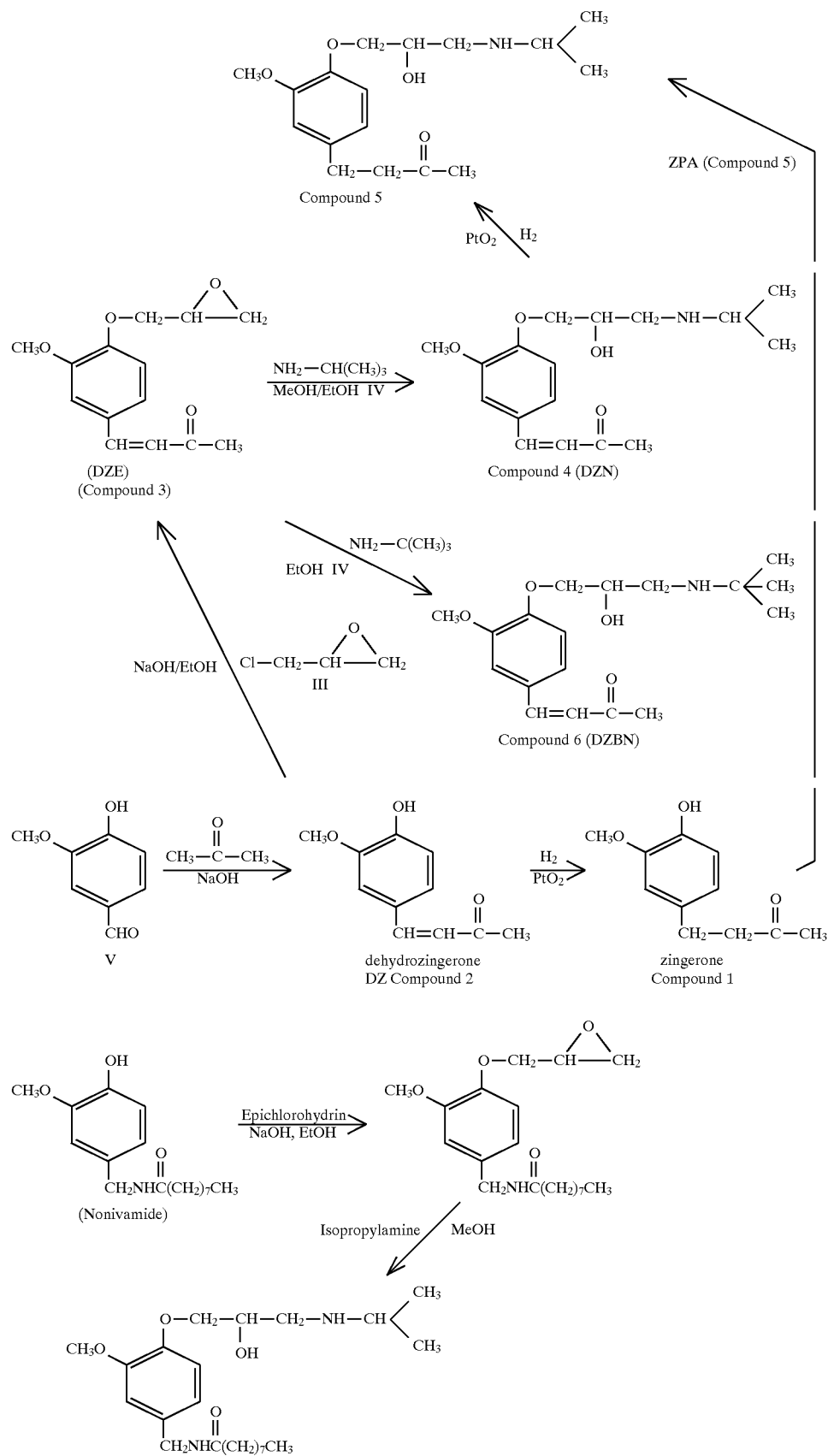

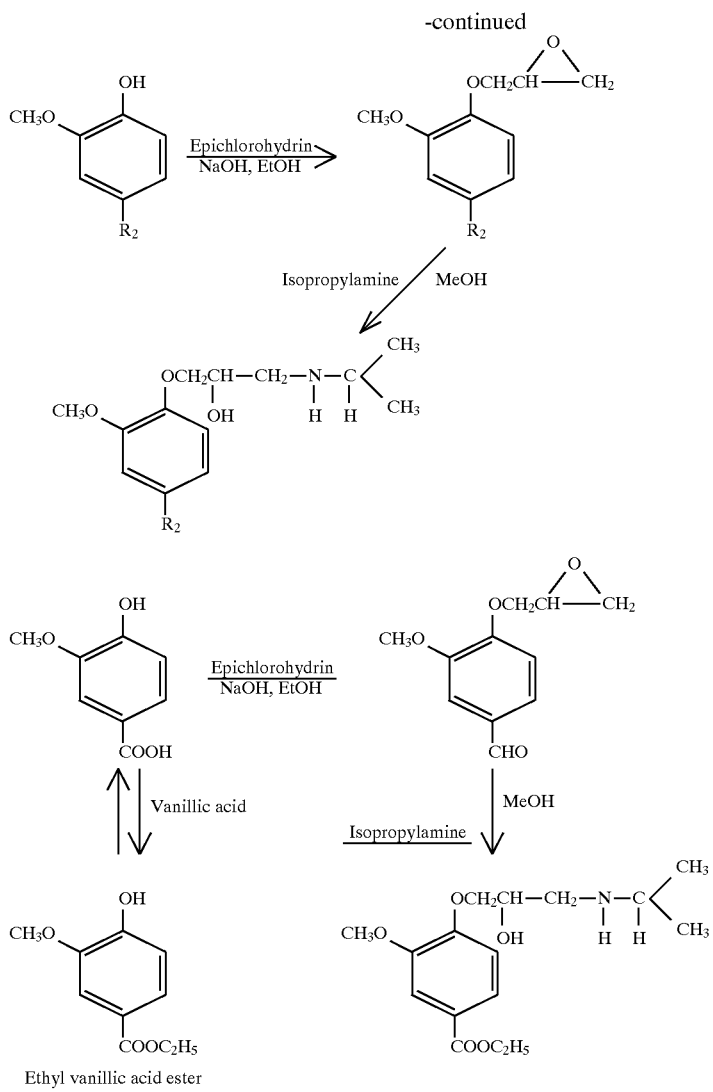

The $R_3$ is a secondary alcohol group with 1 to 6 carbon atoms. $R_4$ is an alkyl group with 1 to 8 carbon atoms and preferably the total number of carbon atoms of $R_3$ and $R_4$ is lower than six. As a suitable base, one may include an inorganic base such as an alkali metal hydride, for instance sodium hydride, or an alkali metal hydroxide, eg. sodium hydroxide, potassium hydroxide, or an alkali metal carbonate, eg. sodium carbonate, or an alkaline earth metal hydroxide, for instance magnesium hydroxide, or the like.

In formula I, the O $R_1$ group may be a methoxy group in the meta position, and $R_2$ on the para position with respect to the O $R_1$ group. The structure of all compounds were supported by data derived from melting points, infrared(IR) and nuclear magnetic resonance (NMR) spectra, mass spectra.

The guaiacoxy- propanolamine derivatives according to the present invention and also their salts display useful pharmacological properties. When $R_1$ is hydrogen, the salts or the compounds are the sodium salts, potassium salts, calcium salts, or magnesium salts. The formula I compounds and their pharmaceutically acceptable salts are selective β-adrenergic blockers, antagonists of platelet aggregation, and β-receptor binding.

The compounds according to this invention are useful as a medicine for the prevention of thrombosis. The following tests are given for the purpose of illustrating the pharmacological activity.

TEST 1

Test Method

The wiping test was performed as described by Szolcsanyiand, Jancso-Gabor. Briefly, the solution or suspension of the test compound and its analogs was made up in 10% ethanol, 5% Tween 80 and then diluted with saline to the required concentrations. Each solution or suspension of $10^{-4}$M, $10^{-3}$M, $10^{-2}$M was dropped into the right eye (vehicle being administered to the left eye as negative control) of male Wistar rats weighing 180–250 g and the total number of protective movements (scratching, wiping of the eye with the foreleg) was counted for 30 minutes. Each test was carried out with a total of 6 rats, and a dose-response curve was obtained from the mean value of each group. MPPs (the concentrations having a moderate pain-producing potency) were calculated from the dose-response curve and those concentrations inducing equal reactions of 32 scratchings were recorded.

Test Compounds 4-(4'-hydroxy-3'-methoxyphenyl)-3-butan-2-one (zingerone,1)

4-(4'-hydroxy-3'-methoxyphenyl)-3-buten-2-one (Dehydrozingerone, DZ,2)

4-[4'-(2,3-Epoxypropoxy)-3'-methoxyphenyl]e-3-buten-2-one (DZE,3)

4-[4'-(2-hydroxy-3-isopropylaminopropoxy)-3'-methoxyphenyl]-3-buten-2-one (DZN, 4)

4-[4'-(2-hydroxy-3-tertbutylaminopropoxy)-3'-methoxyphenyl]-3-buten-2-one(DZBN,6)

Test Result

Based on the obtained MPP values, RPP (relative pain producing potency) values were determined with respect to the pain-producing potency of 1, which was taken as 1000.

4-[4'-(2,3-Epoxypropoxy)-3'-methoxyphenyl)]-3-buten-2-one (DZE,3)

4-[4'-(2-hydroxy-3-isopropylaminopropoxy)-3'-methoxyphenyl]-3-buten-2-one (DZN, 4)

The ED50 values reported in Table 1 show significant variations in antinociceptive effect, zingerone is 3 times more potent than DZ. ED50 is the effective dose for 50% of the animals.

TABLE 1

Comparison of antinociceptive effects of zingerorie analogues on acetic acid-induced writhing syndrome.

| Compound | Dose (mg/kg) | N | Writhes No. (Ave. ± S.E.) | Protection (%) | $ED_{50}$ (95% C.I.) (mg/kg) | Potency ratio |
|---|---|---|---|---|---|---|
| Saline |  | 24 | 80.14 ± 5.13 | 0 |  |  |
| Zingerorie | 0.25 | 8 | 47.13 ± 4.49 | 10.82 | 0.25 (1.06–0.06) | 1.50 |
|  | 1.25 | 8 | 20.75 ± 3.40 | 71.10 |  |  |
|  | 2.50 | 8 | 4.00 ± 2.20 | 95.01 |  |  |
| DZ | 0.25 | 8 | 58.13 ± 5.71 | 27.46 | 0.38 (0.82–0.17) | 1.00 |
|  | 1.25 | 8 | 29.60 ± 3.75 | 63.06 |  |  |
|  | 2.50 | 8 | 2.33 ± 0.83 | 97.09 |  |  |
| DZE | 0.25 | 8 | 46.67 ± 2.09 | 41.76 | 0.23 (0.88–0.06) | 1.70 |
|  | 1.25 | 8 | 27.50 ± 3.32 | 65.69 |  |  |
|  | 2.50 | 8 | 13.86 ± 1.82 | 132.71 |  |  |
| DZN | 0.25 | 8 | 29.80 ± 5.73 | 62.82 | 0.11 (0.60–0.02) | 3.50 |
|  | 1.25 | 8 | 11.17 ± 2.36 | 86.06 |  |  |
|  | 2.50 | 8 | 3.20 ± 0.23 | 96.01 |  |  | a: Writhes were counted for 30 min after acetic acid injection (i.p.)
b: Protection (%) = 100 − (experimental/control × 100)
c: $ED_{50}$'s and 95% confidence intervals were calculated by the Litchfield and Wilcoxon method As shown in FIG. 1, the pain producing potency of compounds 4 and 6 of DZN and DZBN is lower than that of DZ and zingerone.

TEST 2

Test Method

Following the method described by Koster antinociceptive tests were carried out in male mice after intraperitoneal administration of test solution. Briefly, four groups of eight male mice (ddk strain) weighing 18–22 g were brought to the laboratory on the day prior to study, and housed overnight with free access to food and water. Solutions of compound 1 and its analogs as well as indomethacin were made up in 10% ethanol, 10% Tween 80 and 80% saline, and then diluted with saline to the required concentrations. The test solution was administered by intraperitoneal injection of a single dose 0.2 ml (vehicle administered as control). Twenty minutes after injection, 0.2 ml of 0.7% acetic acid was injected intraperitoneally to induce writhing. Following the injection, the mice were placed in separate clear glass cages and the number of writhes was counted for 18 consecutive 5 minute periods beginning 5 minutes after the acetic acid injection, a writhe being defined as a sequence of arching of the back followed by pelvic rotation and hind limb extension.

The compounds tested were:

4-(4'-hydroxy-3'-methoxyphenyl)-3-butan-2-one (zingerone,1)

4-(4'-hydroxy-3'-methoxyphenyl)-3-buten-2-one (Dehydrozingerone DZ,2)

FIG. 2 shows the total numbers of writhes of the compounds tested.

TEST 3

Test Method

Anesthesed rats were administered intravenously DZN (compound 4) in the amounts of 0.1, 0.5, 1.0 mg/kg, Propranolol and isoproterenolol were administered as control. The effect of DZN on heart rate and blood pressure were monitored.

Test Compound

4-[4'-(2-hydroxy-3-isopropylaminopropoxy)-3'-methoxyphenyl]-3buten-2-one (DZN,4)

Test Results (1) As shown in FIGS. 3–6 DZN induced dose-dependent bradycardia and this effect lasted over 1 hr. DZN and propranolol slightly reduced the blood pressure for 5–10 minutes after injection. Statistical significance was not found.

(2) As FIGS. 6(A) and 6(B) show the 0.5 mg/kg isoproterenolol increased the heart rate and decreased blood pressure of rats. Propranolol antagonized the effects of isoproterenolol. These results are in agreement with the findings of Baird, J. R. C. et al (J. Pharm. Pharmac., vol. 24, 880–85, 1972). DZN compound 4 not only reduced resting heart rate but also lowered the blood pressure induced by isoproterenolol.

(3) The $ID_{50}$ value of propranolol induced heart rate change was 0.14 mg/kg, and that of DZN was 0.22 mg/kg (Table 2) calculated by the method of Litchfield, J. L. et al (J. Pharmacol. Exp. Ther., vol. 96, 99–113). The $ID_{50}$ value is the response of a β drug which produces a response in 50% of a drug.

TABLE 2

$ID_{50}$ Heart Rate response of various β-adrenergic blocking agents

| β- Adrenergic blocking agent | $ID_{50}$ : heart rate response (95% C.I.) (mg/kg) |
|---|---|
| Propranolol | 0.14 (0.96–0.02) |
| DZH (compound 4) | 0.22 (1.29–0.04) |

TEST 4

Test Method (1) The test was conducted according to the method described by Malta, E. (BR.J.Pharmac., vol. 85, 179–87, 1985) 0.50 μM of phenoxybenzamine was first applied to the 10 ml organ bath of isolated guinea pig right atrium to block the response of β1 adrenergic receptor. A series of doses of isoproterenolol from $10^{-10}$–$3\times 10^{-8}$M were then introduced into the bath. A bath as described in Gen. Pharmacology 25 p 652 is used to put in the solution of the drug and the organ is hung within the bath and the contraction or relaxation response is shown on a transducer (2) The isolated guinea pig right atrium was pretreated with DZN, and then given isoproterenolol described as above.

Test Compound

4-[4'-(2-hydroxy-3-isopropylaminopropoxy)-3'-methoxyphenyl]-3-buten-2-one (DZN, compound 4)

Test Results (1) The effects of isoproterenolol on contraction force and beating rate of right atrium are dose-dependent. The maximum effect was obtained at $3\times 10^{-8}$M isoproterenolol (FIG. 7).

(2) To obtain the maximum effect of beating rate, a concentration of isoproterenolol is required higher than that of control group (FIGS. 7 and 8). After the treatment with DZN, the sigmoid curve isoproterenolol-dependent concentration effect was partially shifted to the right as shown in FIG. 9. A very close phenomenon was seen when DZN was replaced with propranolol. The estimated $pA_2$ values of DZN and propranolol were 8.16 and 8.36, respectively. Regression analysis revealed a strong correlation between the doses of antagonists and isoproterenolol (FIG. 10).

As described in "Manual of pharmacological calculation with computer programs, New York: Springer Verlag: 1987. by Tallarida, R. J.; Murray, R. B.", the $pA_2$ is a measure of the affinity of a competitive antagonist for its receptor. The determination of the $pA_2$ is made from experiments in which a fixed concentration of the antagonist is used along with graded concentrations of an agonist acting on the same receptor. The presence of the antagonist shifts the agonist dose-response curve to the right.

TEST 5

Test Method (1) The method developed by Piercy, V. et al (J. Pharmac. Methods., vol. 20, 125–33, 1988) was employed for this experiment. Female rats were intraperitonealy injected with stilbestrol (1 mg/kg) to elevate the sensitivity of $β_2$ adrenergic receptor in uterus horns. The rats were subsequently administered reserpine to deplete the catecholamine in uterus. The isolated uterus horns were treated with phenoxybenzamine to block the neuronal uptake and the interaction between neuron cells and the adrenergic receptor.

Test Compound

4-[4'-(2-hydroxy-3-isopropylaminopropoxy)-3'-methoxyphenyl]-3-buten-2-one (DZN,4)

Test results (1) When a krebs' solution was used as the rinsing solution, a fast contraction in the uterus smooth muscle was observed after depolarization, then the muscle relaxed and reached a steady state. Isoproterenolol ranging from $10^{-8}$–$10^{-6}$M was added. A dose-related decrease in relaxation force was observed in the smooth muscle of isolated uterus horns (FIG. 11).

Figure 13:
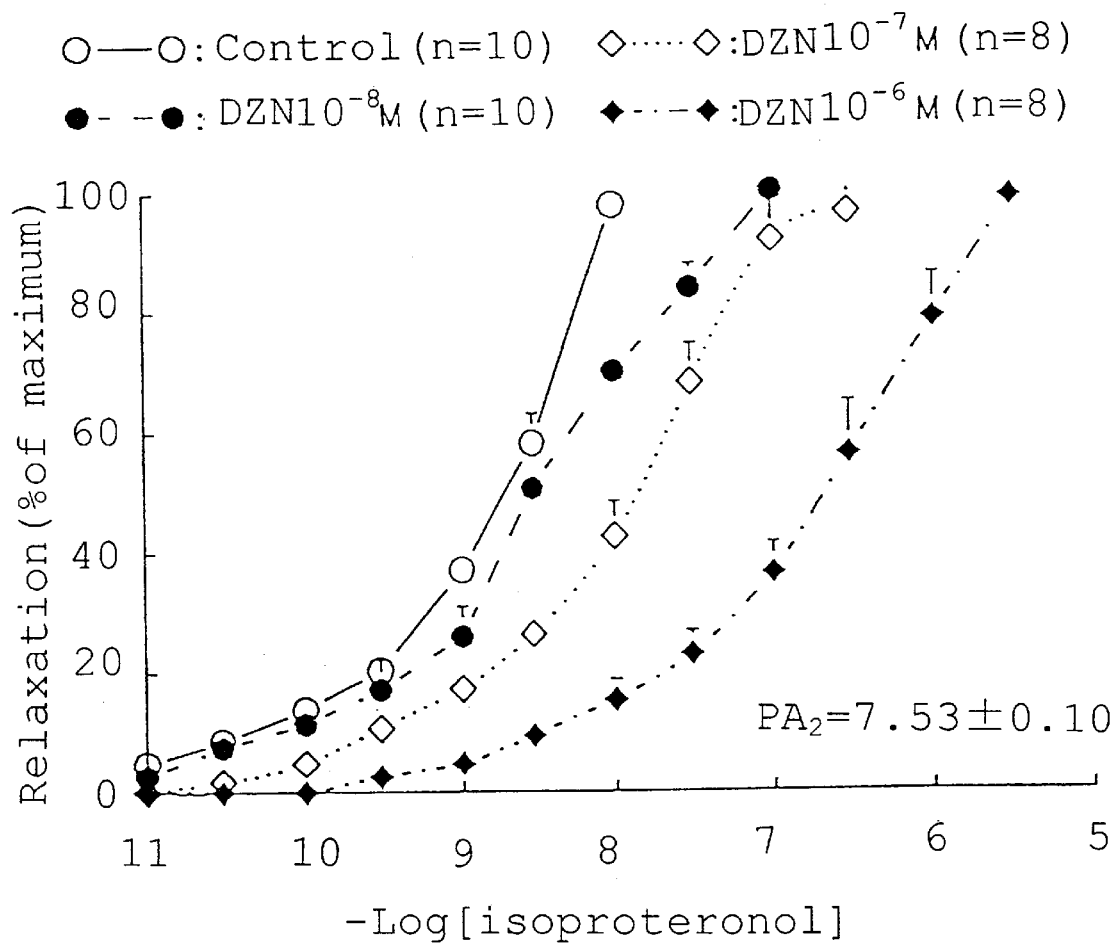

(2) Pretreatment of the isolated uterus horns with $10^{-8}$–$10^{-6}$M DZN caused the concentration of isoproterenolol needed to reach the maximum relaxation effect to be increased as shown in FIGS. 11 and 12. Pretreatment with DZN led the concentration effect curve of isoproterenolol to partially shift to the right (FIG. 13); the $pA_2$ value of DZN was 7.53. The estimated slope of the regression analysis was 0.99±0.11 (FIG. 14).

(3) Compared to isoproterenolol and DZN, propranolol produced a regression slope of 0.99±0.12 and a $pA_2$ values of 8.33 in its concentration-effect curve. As summarized in Table 3, the cardioselectivity of DZN was 4.26 according to the $pA_2$ values obtained from the log concentration-effect curve.

TABLE 3

β-Adrenoceptor blocking potency and cardioselectivity of propranolol and DZN on guinea-pig and rat in vitro preparations. pA2 values and slopes of regression calculated from Schild plots are shown. Cardioselectivity ratio is obtained from the antilogarithm of the difference between the mean pA2 values obtained from different tissues.

| β-Adrenoceptor blocking agent | β1 guinea-pig right atrium (slope) | β2 rat uterus (slope) | Cardioselectivity ratio |
|---|---|---|---|
| Propranolol | 8.36 ± 0.02 (0.97 ± 0.10) | 8.33 ± 0.19 (0.99 ± 0.12) | 1.07 |
| DZN | 8.16 ± 0.03 (0.96 ± 0.05) | 7.53 ± 0.10 (0.99 ± 0.11) | 4.26 |

TEST 6

Test Method

Method of receptor binding assay. After punching the heads of guinea pigs, the blood was drained and the heart ventricle immediately removed. The ventricles were placed in 10 vols. of ice-cold buffer (250 mM sucrose, 1 mM Magnesium Chloride, 50 mM Tris-HCl, pH 7.5) and all subsequent procedures were carried out at 4° C. The ventricles were homogenized using a homogenizer 3–4 times. The period of each homogenization took 15 seconds. The initial homogenate was filtered, and the filtrate was centrifuged at 700 g for 12 minutes. The supernatant was further centrifuged at 10,000 g and the final pellet was resuspended in a small volume of 75 mM Tris buffer containing 25 mM Magnesium Chloride. The membrane protein content was determined by a protein assay dye. The receptor binding assay was initiated by incubating 100 μl of, a membrane protein solution with 50 μl of [$^3$H]-dihydroalprenolol($^3$H-DHA) and the competing drugs. Additional buffer was added to increase the reaction volume up to 250 µl. The binding reaction was activated at 25° C. water by constantly shaking for 60 minutes. The binding reaction was stopped by diluting it with 1 ml of ice-cold assay buffer. The solution was then filtered on a Whatman GF/C glass fiber filter paper under vacuum suction. The filters were washed 3 times with ice-cold assay buffer and dried at 60±C. in an oven for 2 hrs. Then 4 ml of scintillation fluid was added and the radioactivity was counted on β-counter.

Test Compounds

4-[4'-(2-hydroxy-3-isopropylaminopropoxy)-3'-methoxyphenyl]-3-buten-2-one (DZN,4)
4-[4'-(2-hydroxy-3-tert-butylaminopropoxy)-3'-methoxyphenyl]-3-buten-2-one (DZBN,6)
4-[4'-(2-hydroxy-3-isopropylaminopropoxy)-3'-methoxyphonyl]-2-butanone (ZPN,9)

Test Results

Figure 15:
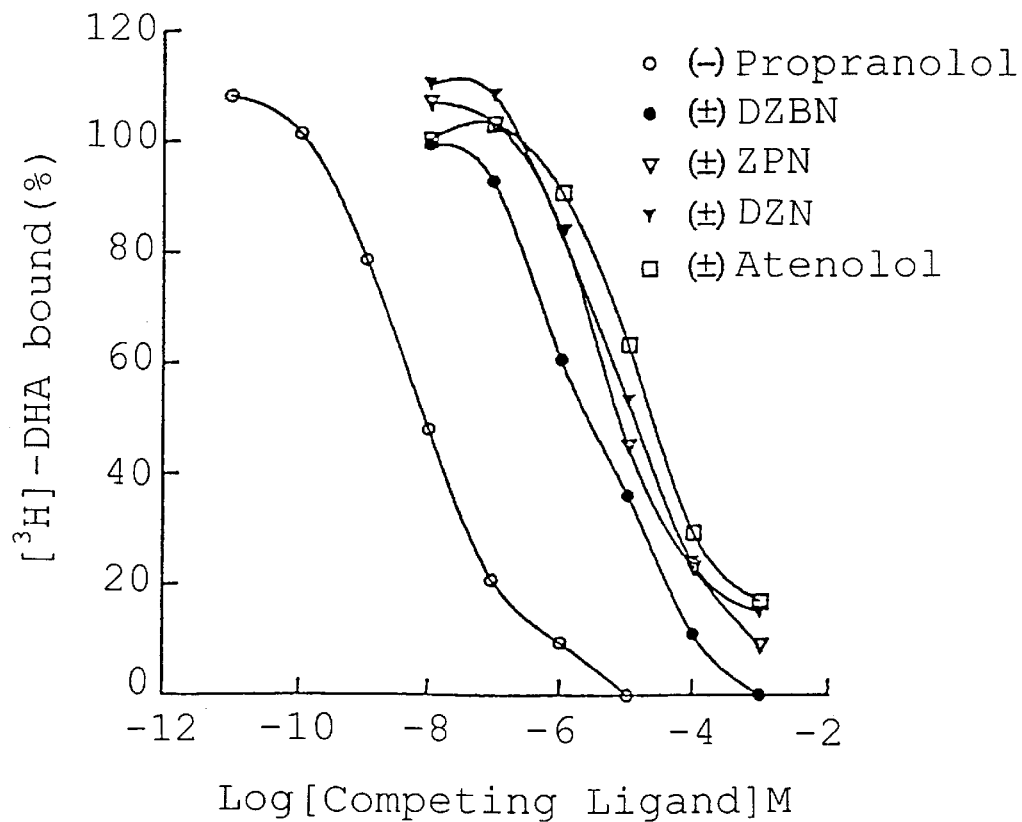

As shown in FIG. 15 and Table 4, the $IC_{50}$ values of DZBN6 and DZN4 are close to the $IC_{50}$ values of the well known β-adrenergic agonist Atenolol. The term $IC_{50}$ is Inhibitory Concentration at 50%, which means the effective concentration of antagonist (or blocker) such as DZBN to inhibit (or decrease) the maximal efficacy of agonist such as isoproterenolol to the half of this maximal efficacy.

TABLE 4

$EC_{50}$ (M) value osf various β-adrenergic antagonists

| β-antagonists | $EC_{50}$ (M) |
|---|---|
| (−)Propranolol | $1.1 \times 10^{-8}$ |
| (±)DZBN | $3.6 \times 10^{-6}$ |
| (±)ZPN | $1,1 \times 10^{-5}$ |
| (±)DZN | $1,3 \times 10^{-6}$ |
| (±)Atenolol | $3.5 \times 10^{-5}$ |

TEST 7

Test

Effect of addition of isoproterenolol in different concentration to the isolated rat right atrium pretreated with reserpine.

Test Compounds 4-(4'-hydroxy-3'-methoxyphenyl)-3-buten-2-one (Dehydrozingerone DZ,2)
4-[4'-(2-hydroxy-3-isopropylaminopropoxy)-3'-methoxyphenyl]-3-buten-2-one (DZN,4)

Figure 16:
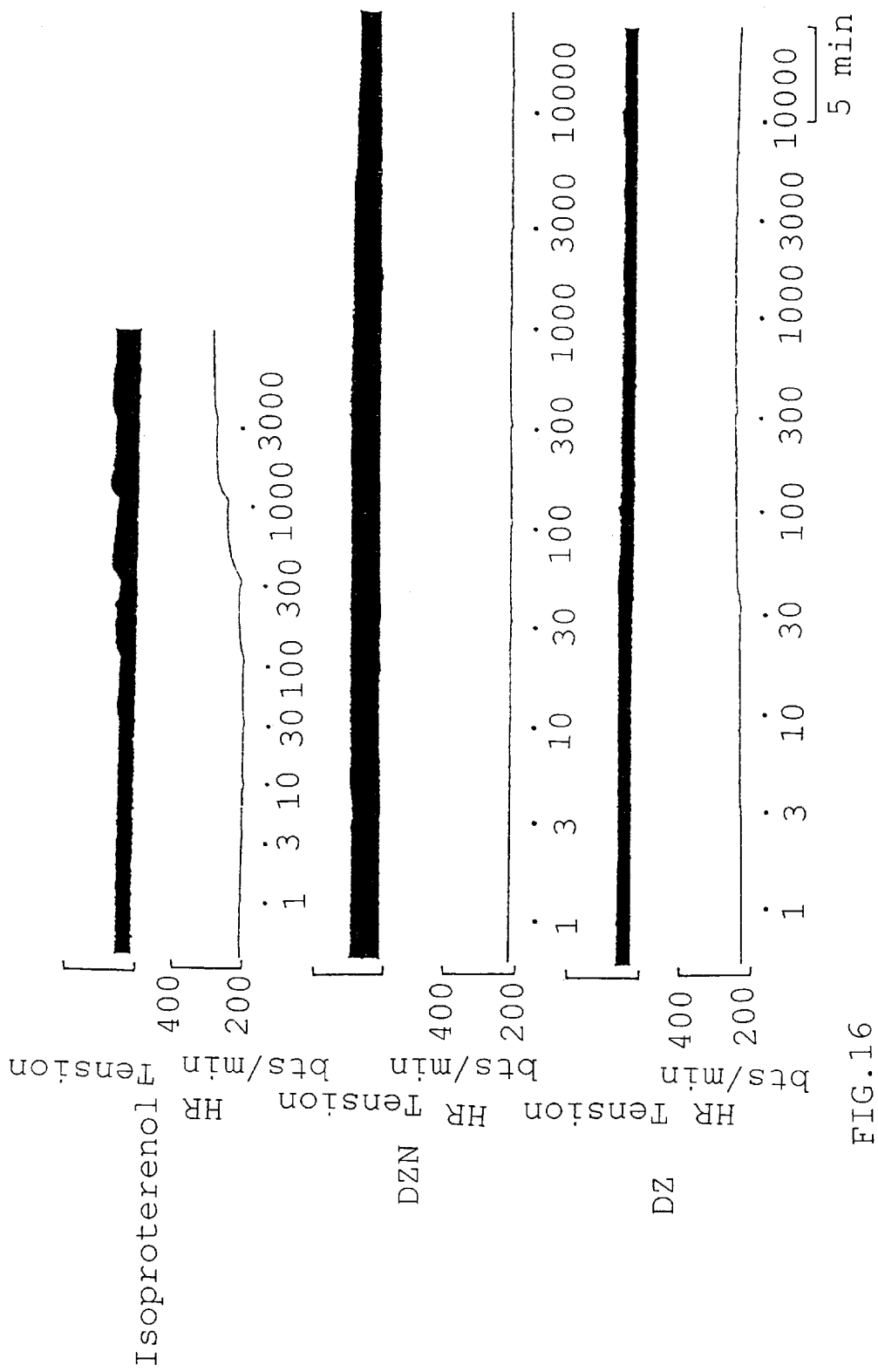

Test Results (1) FIG. 16 shows that isoproterenolol increases the heart rate and contraction force.

Figure 17:
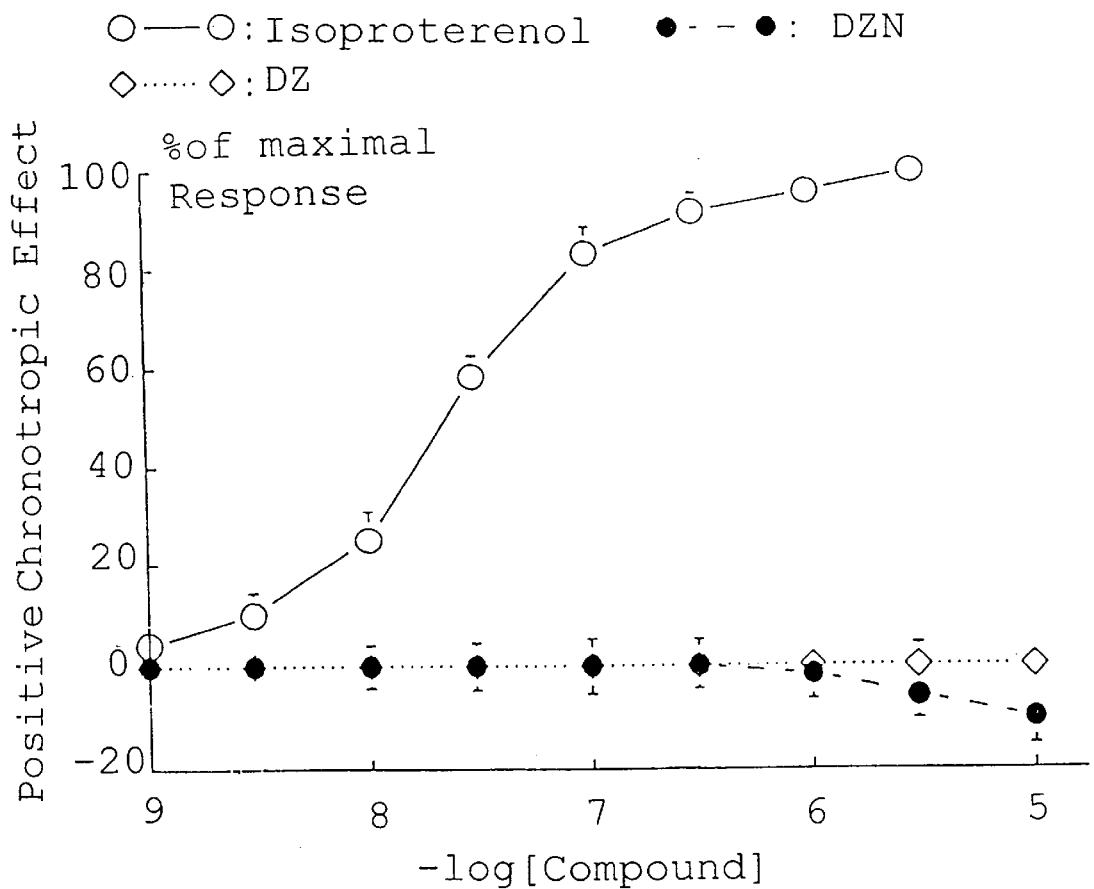

(2) The concentration effect curve indicated that the maximum effect was achieved at $3 \times 10^{-6}$M isoproterenolol (FIG. 17).

(3) The effect of DZN was different from that of isoproterenolol; DZN reduced the heart rate at concentration about $10^{-6}$M. On the other hand, DZ compound 2 did not affect the heart rate within $10^{-9}$–$10^{-5}$M.

TEST 8

Test

The platelet aggregation test was conducted by the method reported by Yeh, H. I. et al (Thromb.Res., vol. 45,39–49, 1987), or Srivastava, K. C. et al (Leuk.Med., vol. 29, 79–84, 1987) as reference.

Test Compounds 4-(4'-hydroxy-3'-methoxyphenyl)-3-butan-2-one (zingerone,1)
4-(4'-hydroxy-3'-methoxyphenyl)-3-buten-2-one (Dehydrozingerone DZ,2)
4-[4'-(2,3-Epoxypropoxy)-3'-methoxyphenyl]-3-buten-2-one (DZE,3)
4-[(4'-(2-hydroxy-3-isopropylaminopropoxy)-3'-methoxyphenyl]-3-buten-2-one (DZN, 4)

Test Results

A monophasic aggregation curve was observed when 10 µg/ml of collagen was added to platelet rich plasma (PRP). Pretreatment of the platelet rich plasma with propranolol, Zingerone, DZ, DZE, and DZN caused a dose-dependent inhibition of platelet aggregation induced by collagen. As seen in FIG. 18, the platelet aggregation was completely inhibited by 250 µM propranolol, 100 µM Zingerone, 250 µM DZ-2, 100 µM DZE-3, 250 µM DZN-4.

TEST 9

Test Method Statistical Methods

The test was conducted according to the method described by Litchfield, J. L. et al (J. Pharmacol.Exp.Ther., vol. 96, 99–113).

The compounds tested were:
4-(4'-hydroxy-3'-methoxyphenyl)-3-buten-2-one (Dehydrozingerone DZ,2)
(4-[4'-(2-hydroxy-3-isopropylaminopropoxy)-3'-methoxyphenyl]-3buten-2-one (DZN,4)

Test Results

The $LD_{50}$'s values are shown in Table 5.

TABLE 5

Acute toxicity of propranolol, DZH and DZ in mice.

| Compound | Route | $LD_{50}$ (95% C.L.)[a] (mg/kg) |
|---|---|---|
| Propranolol | p.o. | 446.92 (303.08–659.04) |
|  | i.p. | 288.79 (200.13–416.72) |
| DZN | p.o. | >1000 |
|  | i.p. | >1000 |
| DZ | p.o. | >1000 |
|  | i.p. | >1000 | a: $LD_{50}$'s and 95% confidence limits were calculated by Litchfield and Wilcoxon method.

The compounds of formula I and their pharmaceutically acceptable acid addition salts can be used as medicaments, eg. in the form of pharmaceutical preparations for enteral, parenteral, topical or oral application. The manufacture of the pharmaceutical compositions may be carried out in a manner which is familiar to any person skilled in the art by using the described compounds of formula I and their pharmaceutically acceptable acid addition salts, optionally in combination with other therapeutically valuable subcutaneous substances such as corn starch, starch, lactose, sodium carboxymethylcellulose, ethanol. The β-adrenergic blocker compositions to be used orally contain about 60 mgs. per dose of a compound according to the present invention.

Vaninolol of formula hereinbelow

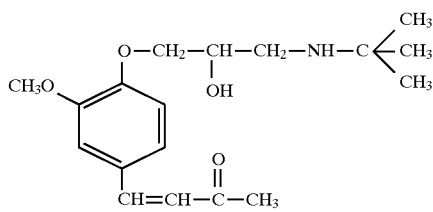

has been shown to lower the intraocular pressure (IOP) and is useful in the treatment of glaucoma in the form of an eye solution.

This 4-[4'-(2-hydroxy-3-tert-butylaminopropoxy)-3'-methoxyphenyl]-3-buten-2-one (DZBN) compound 6 is watersoluble and exhibits lower pungency so that it is preferred for parenteral and eye solution. The preferred individual dosage is 0.25 %, 0.5% eye solution and may be administered up to twice daily.

The following examples and preparation are given for the purpose of illustration of this invention.

EXAMPLE 1

(Dehydrozingerone, DZ,2)

Aqueous sodium hydroxide 30% was slowly added to 50 g vanillin at a temperature lower than 25° C. After the dropwise addition of 7 mole acetone, the heterogeneous mixture was stirred for a further 48 hours. The solution was then treated with hydrochloric acid until the pH was 6.5 and was allowed to stand overnight until a precipitate separated. The solution was filtered and the filtrate was evaporated. The residue is recrystallized from methanol to give 4-(4'-hydroxy-3'-methoxyphenyl)-3-buten-2-2one (Dehydrozingerone,-DZ,2) as yellow crystal.

mp: 125°–126° C.

UV λmax nm (log ε): 241.5(4.12),337(4.43).

$^1$H-NMR(CDCl$_3$): δ7.46(d,1H, CH=CH), 6.92–7.14(m, 3H, Ar), 6.59(d,1H, Ar—CH), 6.25(s,1H, OH), 3.93(s,3H, OCH$_3$), 2.37(s, 3H, CH$_3$).

IR (KBr): 1650 cm$^{-1}$(carbonyl,C=0),1595 cm$^{-1}$ (conjugated C=C).

FAB-MS m/z: 193[M+H]$^+$.

Anal(C$_{11}$H$_{12}$O$_3$) C.H.

EXAMPLE 2

4-[4'1-(2,3-Epoxypropoxy)-3'-methoxyphenyl]-3-buten-2-one (DZE,3)

20 g Dehydrozingerone and 4 g NaOH were dissolved under stirring in absoluted ethanol overnight. Then 5 ml chlorohydrin was added and then heated. After cooling, the inorganic salt was filtered off, the filtrate was diluted with methanol, and then treated with conc. HCl to pH 7.0. The separated solid was recrystallized from ethanol to afford 4-[4'-(2,3-epoxypropoxy)-3'-methoxyphenyl]-3 buten-2-one (DZE, 3) 75% as colorless needles.

mp: 123°–124° C.

UV λmax nm (log ε): 239.5(4.16), 331(4.41).

$^1$H-NMR(CDCl$_3$): δ7.42–7.50 (d,1H, CH=CH), 6.92–14 (m,3H, Ar 6.57–6.65 (d,1H, Ar—CH), 4.02–4.37(m,2H, CH$_2$OAr), 3.92(s,3H, OCH$_3$), 3.40–3.42(br s,1H, CHO), 2.75–2.95(m,2H, CH$_2$ of the epoxide), 2.38(s,3H, CH$_3$).

IR (KBr): 1650 cm$^{-1}$(carbonyl, C=0).

FAB-MS m/z: 249[M+H]$^+$.

Anal(C$_{14}$H$_{16}$O$_4$) C.H.

EXAMPLE 3

4-[4'-(2-hydroxy-3-isopropylaminopropoxy)-3'-methoxyphenyl]-3-buten-2-one(DZN,4)

To 10 ml of isopropylamine were added 10 g of DZE (3) and 50 ml ethanol. The mixture was heated under reflux at 55° C. for 1 hr. The mixture was then evaporated in a rotary evaporator. The residue was extracted with ether, and recrystallized from benzene to give 4-[4'-(2-hydroxy-3-isopropylaminopropoxy)-3'-methoxyphenyl]-3-buten-2-one (DZN,4) 45%, as pale yellow crystals.

mp: 109°–110° C.;

UV λmax nm (log ε): 330(4.39).

$^1$H-NMR(CDCl$_3$): δ42–7.50(d,1H, CH=CH), 6.89–7.08 (M,3H, Ar), 6.56–6.65 (d,1H, Ar—CH), 4.07(m,3H, OCH$_2$CHO), 3.89(s,9,3H, OCH$_3$), 2.80–2.86(s,3H, CH$_2$NHCH), 2.57(br s,2H, exchangeable OH & NH), 2.37 (s,3H, CH$_3$), 1.08–1.11(d,6H, CHMe$_2$) °

IR (KBr): 3300 cm$^{-1}$ amine(N–H), 1650 cm$^{-1}$ carbonyl (C=0).

FAB-Ms m/z: 308[M+H]$^+$.

Anal(C$_{17}$H$_{25}$NO$_4$) C.H.N.

EXAMPLE 4

4-[4'-(2-hydroxy-3-(isopropylaminopropoxy)-3'-methoxyphenyl]-2-butanone (ZPN,5)

1 g DZN (compound 4) was dissolved in ethanol and reduced with hydrogen using platinum oxide as catalyst 70° C. and 60 p.s.i. After filtering off the platinum oxide, the filtrate was evaporated and recrystallized from methanol to afford 4-[4'-(2-hydroxy-3-(isopropyamino)propoxy)-3'-methoxyphenyl]-2-butanone ZPN,5) 90% as pale yellow crystals, $^1$H-NMR(CDCl$_3$): δ6.68–6.86(m,3H, Ar), 4.07(m,3H, OCH$_2$CH), 3.85(s,3H, OCH$_3$), 2.74–2.88(m,7H, CH$_2$CH$_2$&CH$_2$NHCH), 2.15(s,3H, CH$_3$), 1.10–1.13(d,6H, CHMe$_2$).

FAB-MS m/z: 310[M+H]$^+$.

Anal (C$_{17}$H$_{27}$NO$_4$) C.H.N.

EXAMPLE 5

4-[4'-(2-hydroxy-3-tert-butylaminopropoxy)-3'-methoxyphenyl]-3-buten-2-one(DZBN,6)

To 10 ml of tert-butylamine were added 100 g of DZE(3) and 50 ml of absoluted methanol. The mixture was heated under nitrogen at 55° C. reflux for 2 hrs. The mixture was evaporated in a rotary evaporator and then dichloromethane (CH$_2$Cl$_2$) was added and let stand overnight. The precipitate which separated was filtered off and recrystallized from CH$_2$Cl$_2$ to give 4-[4'-(2-hydroxy-3-tert-butylaminopropoxy) -3'-methoxyphenyl]-2-butenone (DZBN, 6) 75% as pale yellow crystals.

mp 96°–97° C.

$^1$H-NMR(CDCl$_3$): δ7.52–7.60(d,1H, C=CHCO), 7.07–7.45(m,3H, Ar), 6.7–6.8(d,1H, ArCH), 4.98(br,1H, OH), 3.9–4.05(m, ArOCH$_2$CH), 3.8(s,3H, OCH$_3$), 2.5–2.7 (m,3H, CH$_2$NCH), 2.3(s,3H, COCH$_3$), 1.03(s,9H, CH$_3$×3).

IR (kBr): 3300, 1690, 1595, 1510, 1270, 1150, 810 cm$^{-1}$

FAB-MS m/z: 322[M+H]$^+$.

Anal($C_{18}H_{27}NO_4$) C.H.N.

EXAMPLE 6

N-[4-0-(2-hydroxy-3(isopropylamine)propoxy)-3-methoxyphenyl]-2-propylene 8 g sodium hydroxide was dissolved in 130 ml ethanol and then were added 80 ml epichlorohydrin and 38 g Eugenol. The mixture was heated under 70° C. for 1.5 hrs, after cooling, it was reacted with 50 ml isopropylamine. The precipitate solid product is filtered off and recrystallized from ethylacetate to afford N-[4-0-(2-hydroxy-3 (isopropylamine) propoxy)-3-methoxyphenyl]-2-propylene 85% as colorless crystals.

mp 63°–64° C., $^1$H-NMR, CDCl$_3$: δ1.06(d,6H,CH$_3$×2), 1.98(br 1H,OH, exchangable), 2.6–2.9(m, 3H,CH$_2$—N—CH), 3.35(d,2H, ArCH$_2$), 3.85(S,3H,OCH$_3$), 3.9–4.1(m,3H,—CH—CH$_2$—O), 5.03–5.14(m,2H, —C=CH$_2$), 5.85–6.1(m,1H,HC=C), 6.7–6.9(m,2H,Ar).

IR (kBr): 3400, 3300, 1525, 1475, 1250, 1040 cm$_{-1}$.

Anal($C_{16}H_{25}NO_3$) C.H.N

EXAMPLE 7

N-([4-o-(2,3-epoxypropoxy)-3-methoxy benzyl]-nonamide,NVAE)

Three grams of sodium hydroxide was dissolved in 60 ml ethanol and 30 ml epichlorohydrin and 10 g (34 m mol) nonivamide were added. The mixture was heated at a temperature lower than 80° C. for 3 hrs. The filtrate was evaporated and recrystallized from absoluted ethanol to give N-[4-o-(2,3-epoxypropoxy)-3-methoxy benzyl]-nonamide, NVAE) 85% as colorless crystals.

mp 124°–125° C.

UV λmax nm (log ε): 228.5(3.98), 278(3.48).

$^1$H-HMR (CDCl$_3$): δ0.87(t,3H,CH$_3$), 1.26(m,10H,CH$_2$× 5), 1.65(s,2H,CH$_2$×1), 2.20(t,2H,CH$_2$×1), 2.74–2.90(m,2H, epoxy CH$_2$), 3.36(br s,1H,epoxy CH$_2$), 3.86(s,3H, OCH$_3$), 4.03–4.12(dd,2H,Ar—CH$_2$), 4.36(d,2H,Ar—CH$_2$), 5.71(s, 1H,NH), 6.81–6.91(m,3H,Ar).

IR (KBr) 1640, 1600, 1220 (cm$_{-1}$).

FAB-MS m/z: 349[M]$_+$.

Anal($C_{20}H_{31}NO_1$) C.H.N.

The following compounds were prepared in the same manner as described hereinabove.

EXAMPLE 8

N-[4-o-(2-hydroxy-3-(isopropylamino)propoxy)-3-methoxybenzyl]-nonamide, NVAEN)

mp: 120°–121° C.

UV λmax nm (log ε): 228.5(3.95), 278(3.47).

$^1$H-NMR(CDCl$_3$): δ0.87(t,3H,CH$_3$), 1.11(d,6H,CH$_3$×2), 1.26–2.24(m,14H, CH$_2$×7), 2.54(br s,1H,exchangeable, OH), 2.70–2.90(m,3 h,CH$_2$—NH—CH) 3.83(s,3H,OCH$_3$), 3.95–4.06(m,3H,Ar—OCH$_2$—CH(OH)—), 4.35(d,2H, Ar—CH$_2$), 5.71(s,1H,NH), 6.81–6.91(m,3H,Ar).

IR (KBr): 3400,1640 cm$_{-1}$.

FAB-MS m/zs: 408[M]$_+$.

Anal($C_{23}H_{40}N_2O_4$) C.H.N.

EXAMPLE 9

N-[4-o-(2-hydroxy-3-(n-propylamino)propoxy)-3-methoxybenzyl]-nonamide mp: 132°–133° C.

UV λmax nm (log ε): 228(4.23), 277.5(3.73);

$^1$H-NMR(CDCl$_3$): δ0.99 (s,3H,—CH$_3$), 1.85–1.95(qt,2H, —CH$_2$—CH$_3$), 3.05(br s,1H,exchangeable, OH), 3.03–3.38 (m,4H,CH$_2$—NH—CH$_2$), 4.02(m,3H,Ar—OCH$_2$—CH (OH)—), FAB-MS m/z: 408[M]$_+$.

Anal($C_{23}H_{40}O_4$) C.H.N.

EXAMPLE 10

N-[4-o-(2-hydroxy-3-(methylamino)propoxy)-3-methoxybenzyl]-nonamide mp: 101°–104° C.

UV λmax nm (log ε): 229(3.70), 278(3.38);

$^1$H-NMR(CDCl$_3$): δ1.96(br s,1H,exchangeable,OH), 2.47 (s,3H,NH—CH$_3$), 2.79(dd,2H,—CH$_2$—NH), 4.01(d,2H, Ar—OCH$_2$), 4.08(m,1H,—CH(OH)—), 5.69(s,1H,NH).

PAB-HS m/z: 380[M]$_+$.

Anal($C_{21}H_{36}N_2O_4$) C.H.N.

EXAMPLE 11

N-[4-o-(2-hydroxy-3-(ethylamino)propoxy)-3-methoxybenzyl]-nonamide mp: 102°–103° C.

UV λmax nm (log ε): 229(3.72), 278.5(3.27);

$^1$H-NMR(CDCl$_3$): δ1.12(t,3H,—CH$_3$), 2.62(br s,1H, exchangeable,OH), 2.63–2.83(m,4H,—CH$_2$—NH—CH$_2$), 3.98(d,2H,Ar—OCH2), 4.05(m,1H,—CH(OH)—), 5.88(s, 1H,NH).

FAB-MS m/z: 393[M]$_+$.

Anal($C_{23}H_{38}N_2O_4$) C.H.N.

EXAMPLE 12

N-[4-0-(2-hydroxy-3-(allylamino)propoxy)-3-methoxybenzyl]-nonamide mp: 98°–99° C.

UV λmax nm (log ε): 228.5(4.18), 278(3.69);

$^1$H-NMR(CDCl$_3$): δ2.40(br s,1H,exchangeable,OH), 2.82 (m,2H,—(OH)CH—CH$_2$—NH—), 3.28(dt,2H,—NH—CH$_2$—CH=), 4.02(m,3H,Ar—OCH$_2$—CH(OH)—), 5.15 (m,2H,—CH=CH$_2$), 5.77(s,1H,NH), 5.89(m,1H,—CH=CH$_2$)

FAB-HS m/z: 406[M]$_+$.

Anal($C_{23}H_{38}N_2O_4$) C.H.N.

EXAMPLE 13

N-[4-o-(2-hydroxy-3-(cyclopropylamino)propoxy)-3-methoxybenzyl]-nonamide mp: 95°–99° C.

UV λmax nm (log ε): 227(3.71), 278(3.30);

$^1$H-NMR(CDCl$_3$): δ0.40(m,4H, —CH$_2$—CH$_2$—), 2.19 (m,1H,—NH—CH), 2.33(br s,1H,exchangeable,OH 2.90

(m,2H,—CH—CH$_2$—NH—), 4.12(m,3H, Ar—OCH$_2$—CH(OH)—), 5.77(s,1H,NH).

FAB-HS m/z: 406[M]$_+$.

Anal(C$_{23}$H$_{38}$N$_2$O$_4$) C.H.N.

EXAMPLE 14

N-[4-o-(2-hydroxy-3-(n-butylamino)propoxy)-3-methoxybenzyl]-nonamide mp: 97°–101° C.

UV λmax nm (log ε): 227(4.21), 278(3.74);

$^1$H-NMR(CDCl$_3$): δ0.95(s, 3H, —CH$_3$), 1.45(m,4H, CH$_2$×2), 2.42(br s,1H,exchangeable,OH), 2.63(t,2H,—NH—CH$_2$—), 2.80(m,2H,—CH$_2$—NH—), 4.02 (m,3H, Ar—OCH$_2$—CH(OH)—), 5.78(s,1H,NH).

FAB-MS m/z: 422[M]$_+$.

Anal(C$_{24}$H$_{42}$N$_2$O$_4$) C.H.N.

EXAMPLE 15

N-[4-o-(2-hydroxy-3-(iso-butylamino)propoxy)-3-methoxybenzyl]-nonamide mp: 98°–102° C.

UV λmax nm (log ε): 227(4.20), 278(3.72);

$^1$H-NMR(CDCl$_3$): δ0.94(s,6H,CH$_3$×2), 1.75(m,1H,NH—CH$_2$—CH—), 2.12(br s,1H,exchangeable,OH), 2.46(d,2H,—NH—CH$_2$—CH—), 2.80(m,2H,—CH$_2$—NH—), 4.04 (m,3H,Ar—OCH$_2$—CH(OH)—), 5.78(s,1H,NH).

FAB-MS m/z: 422[M]$_+$.

Anal(C$_{24}$H$_{42}$N$_2$O$_4$) C.H.N.

EXAMPLE 16

N-[4-o-(2-hydroxy-3-(sec-butylamino)propoxy)-3-methoxybenzyl]-nonamide mp: 97°–101° C.

UV λmax nm (log ε): 228(4.28), 278(3.82).

$^1$H-NMR(CDCl$_3$): δ60.94(m,3H,—CH$_3$), 1.05(d,3H,—CH(CH$_3$)—), 2.16(br s,1H,exchangeable,OH), 2.65(m,1H, —NH—CH—), 2.80(m,2H,—(OH)CH—CH$_2$—NH—), 4.02(m,3H,Ar—OCH$_2$—CH(OH)—), 5.78(s,1H,NH).

FAB-MB m/z: 422[M]$_+$.

Anal(C$_{24}$H$_{42}$N$_2$O$_4$) C.H.N.

EXAMPLE 17

N-[4-o-(2-hydroxy-3-(tert-butylamino)propoxy)-3-methoxybenzyl]-nonamide mp: 95°–96° C.

UV λmax nm (log ε): 228(3.51), 277.5(3.01);

$^1$H-NMR(CDCl$_3$): δ1.12(s,9H,—CH$_3$×3), 2.47(br s,1H, exchangeable,OH), 2.75(m,2H, —CH$_2$—NH—C), 3.99(m, 3H,Ar—OCH$_2$—CH(OH), 5.77(s,1H,NH).

FAB-MS m/z: 422[M]$_+$.

Anal(C$_{24}$H$_{42}$N$_2$O$_4$) C.H.N.

EXAMPLE 18

N-[4-o-(2-hydroxy-3-(n-pentylamino)propoxy)-3-methoxybenzyl]-nonamide mp: 95°–99° C.

UV λmax nm (log ε): 228(3.56), 278(3.10);

$^1$H-NMR(CDCl$_3$): δ0.87(m,3H,—CH$_3$), 1.26(m,4H,—CH$_2$×2), 1.49(t,2H,CH$_2$×2), 2.75(br s,1H,exchangeable, OH), 2.60–2.82(m,4H,CH$_2$—NH—CH$_2$), 3.99(m,3H,Ar—OCH$_2$—CH(OH)—), 5.91(s,1H,NH).

FAB-HS m/z: 436[M]$_+$.

Anal(C$_{26}$H$_{44}$N$_2$O$_4$) C.H.N.

EXAMPLE 19

N-[4-0-(2-hydroxy-3-(3-aminopentylamino)propoxy)-3-methoxybenzyl-]-nonamide mp: 97°–101 ° C.

UV λmax nm (log ε): 227(4.16), 278(3.72);

$^1$H-NMR(CDCl$_3$): δ0.88(m,6H,—CH$_3$×2), 1.42(m,4H,—CH$_2$×2), 2.42(br s,1H, exchangeable,OH), 2.37(m,1H,—NH—CH), 2.82(m,2H,—CH$_2$—NH—), 4.00(m,3H,Ar—OCH$_2$—CH(OH)—), 5.81(s,1H,NH).

FAB-MS m/z: 436[M]$_+$.

Anal(C$_{26}$H$_{44}$N$_2$O$_4$) C.H.N.

EXAMPLE 20

N-[4-o-(2-hydroxy-3-(n-hexylamino)propoxy)-3-methoxybenzyl]-nonamide mp: 93°–97° C.

UV λmax nm (log ε): 227(4.17), 278(3.74);

$^1$H-NMR(CDCl$_3$): δ0.87(m,3H,—CH$_3$), 1.26(m,4H,—CH$_2$×2), 1.49(t,2H,CH$_2$×1), 2.75(br s,1H,exchangeable, OH), 2.60–2.82(m,4H,CH$_2$—NH—CH$_2$), 3.99(m,3H,Ar—OCH$_2$—CH(OH)—), 5.91(s,1H,NH).

FAB-MS m/z: 450[M]$_+$.

Anal(C$_{26}$H$_{46}$N$_2$O$_4$) C.H.N.

EXAMPLE 21

N-[4-o-(2-hydroxy-3-(cyclohexylamino)propoxy)-3-methoxybenzyl]-nonamide mp: 95°–99° C.

UV λmax nm (log ε): 227(4.15), 278(3.74);

$_1$H-NMR(CDCl$_3$): δ1.26(s,4H,—CH$_2$×2), 1.67(m,4H,—CH$_2$×2), 1.90(d,2H,—CH$_2$×1), 2.21(br s,1exchangeable, OH), 2.43(m,1H,—NH—CH), 2.87(m,4H,—CH$_2$—NH—), 3.99(m,3H,Ar—OCH$_2$—CH(OH)—), 5.76(s,1H,NH).

FAB-MS m/z: 448[M]$_+$.

Anal(C$_{26}$H$_{44}$N$_2$O$_4$) C.H.N.

EXAMPLE 22

N-[4-o-(2-hydroxy-3-(n-heptylamino)propoxy)-3-methoxybenzyl]-nonamide mp: 93°–97° C.

UV λmax nm (log ε): 227(3.86), 278(3.42);

$^1$H-NMR(CDCl$_3$): δ0.88(m,3H,—CH$_3$), 1.26(s,8H,—CH$_2$×4), 1.48(t,2H,—CH$_2$×1), 2.05(br s,1H,exchangeable, OH), 2.68(dd,2H,—NH—CH$_2$—), 2.81(m,2H,—CH$_2$—NH—), 4.08(m, 3H,Ar—OCH$_2$—CH(OH )—), 5.78(s,1H, NH).

FAB-MS m/z: 464[M]$_+$.

Anal(C$_{27}$H$_{48}$N$_2$O$_4$)

EXAMPLE 23

N-[4-o-(2-hydroxy-3-(benzylamino)propoxy)-3-methoxybenzyl]-nonamide mp: 96°–102° C.

UV λmax nm (log ε): 227(4.17), 278(3.72).

$^1$-NMR(CDCl$_3$): δ2.58(br s,1H,exchangeable,OH), 2.85 (m,2H,—CH$_2$—NH—), 3.81(d,2H,—NH—CH$_2$—Ar), 4.01 (m,3H,Ar—OCH$_2$—CH(OH)—), 5.82(s,1H,NH), 7.33(m, 3H,—Ar).

FAB-MS m/z: 456[M]$_+$.

Anal(C$_{27}$H$_{40}$N$_2$O$_4$) C.H.M.

EXAMPLE 24

N-(4-O-dimethylaminoethyl-3-methoxybenzyl)-nonamide mp 78°–80° C.

UV λmax nm (log ε): 201(5.47);

$^1$H-NMR(CDCl$_3$): δ0.87(t,3H,CH$_3$), 1.20–2.25(m,14H, CH$_2$×7), 2.39–2.43(s,6H,(CH$_3$)$_2$N), 2.8–2.9(t,2H,NCH$_2$), 3.85(s,3H,OCH$_3$), 4.13(t,2H, OCH$_2$), 4.36–4.40(d,2H, ArCH$_2$), 5.70(br,1H,NH), 6.81–6.83(m,3H,Ar).

IR (KBr): 3300, 3100, 2800–3000, 1600, 1500, 1200, 650 cm$_{-1}$.

FAB-MS m/x: 364[M]$_+$.

Anal (C$_{21}$H$_{34}$N$_2$O$_3$) C.H.N.

EXAMPLE 25

N-(4-o-4diethylaminoethyl-3-methoxybenzyl)-nonamide mp: 51°–53° C.

UV λmax nm (log ε): 201(5.14).

$^1$H-NMR (CDCl$_3$): δ0.87(t,3H,CH$_3$), 1.05–1.13(t,6H, CH$_3$×2), 1.20–2.25(m,14H,CH$_2$×7), 2.60–2.75(q,4H,(CH$_2$)$_2$N) 2.95–3.0(t,2H,NCH$_2$), 3.85(s,3H,OCH$_3$), 4.11(t,2H, OCH$_2$), 4.32–4.40(d,2H, ArCH$_2$), 5.70(br,1H,NH), 6.78–6.90(m,3H,Ar).

IR (KBr) 3300, 2800–3000, 1620, 1520, 800, 650 cm$_{-1}$.

FAB-MS m/z: 392[M]$_+$.

Anal(C$_{23}$H$_{40}$N$_2$O$_3$) C.H.N.

EXAMPLE 26

N-(4-O-pyridylmethyl-3-methoxybenzyl)-nonamide mp: 99°–101° C.

UV λmax nm (log ε): 280(4.15), 314(3.18), 327(3.20).

$^1$H-NMR(CDCl$_3$): δ0.86(m,3H,CH), 1.25–2.22(m,14H, CH$_2$×7), 3.5(s,3H,OCH$_3$), 3.9(s,2H,NCH$_2$—Ar), 4.5(d,2H, OCH—Ar), 5.3(s,1H,CONH), 6.8(m,3H,Ar), 7.2–7.8(m, 4H,Ar).

IR (KBr): 3300, 2850–3000, 1620, 1525, 1280, 800, 750 cm$_{-1}$

FAB-MS m/z: 385[M]$_-$.

Anal(C$_{23}$H$_{33}$O$_3$N$_3$)

EXAMPLE 27

N-(4-O-piperidylethyl-3-methoxybenzyl)-nonamide mp: 77°–78° C.

UV λmax nm (log ε): 280(3.50).

$^1$H-NMR(CDCl$_3$): δ0.8–0.9(t,3H,CH$_3$), 1.2–1.6(m,6H, CH$_2$×3), 1.2–2.8(m,14H,CH$_2$×7), 3.4(m,3H,CH$_2$NCH), 3.7 (s,3H,OCH$_3$), 4.0–4.2(m,2H,OCH$_3$), 6.7–6.8(m,3H,Ar), 8.2 (s,1H,CONH).

IR (KBr): 3300, 2850–3000, 1620, 1510, 1220, 800, 750 cm$_{-1}$.

FAB-MS m/z: 403[M]$_+$.

Anal(C$_{24}$H$_{39}$N$_2$O$_3$) C.H.N.

EXAMPLE 28

A 0.5% drop eye solution is prepared, for example, as follows.

dehydrozingerone(DZ) 500 mg

NaCl 0.9% 100 C.C

EXAMPLE 29

A 0.25% drop eye solution is prepared, for example, as follows.

DZBN(6) 250 mg

NaCl 0.9% 100 C.C

TABLES 6 and 7 Summarize the Properties of the Guaiacoxypropanolamines of the Present Invention

TABLE 6

Heart Rate and Blood Pressure Changes of Rats Induced by Guaiacoxypropanolamines

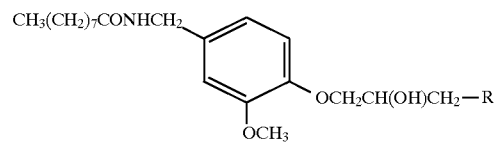

change in BP (mmHg) or HR (beats/min) at the following times after dosing[a]

| R | | 5 min | 10 min | 15 min | 30 min | 60 min |
|---|---|---|---|---|---|---|
| NHCH$_3$ | BP | −1.11 ± 2.31 | −0.22 ± 2.10 | −0.56 ± 1.65 | 1.89 ± 2.14 | 0.78 ± 1.37 |
|  | HR | −34.56 ± 6.79[c] | −17.33 ± 5.31[b] | −12.22 ± 4.33 | 14.56 ± 7.73 | 4.78 ± 4.37 |
| NHC$_2$H$_5$ | BP | 7.44 ± 3.16 | 2.56 ± 2.56 | 1.11 ± 1.78 | −2.44 ± 3.05 | 1.88 ± 1.62 |
|  | HR | −38.33 ± 5.94[c] | −32.22 ± 5.36[c] | −28.00 ± 7.02[b] | −21.11 ± 8.75 | 2.56 ± 11.66 |
| NHC$_3$H$_5$ | BP | −1.56 ± 2.03 | −2.67 ± 1.96 | −1.89 ± 2.04 | −1.11 ± 2.62 | 4.78 ± 4.96 |
|  | HR | −36.78 ± 11.25[b] | −28.22 ± 9.00[b] | −19.89 ± 9.26 | −5.00 ± 8.72 | −7.56 ± 4.14 |
| NH-c-C$_3$H$_5$ | BP | −0.11 ± 1.09 | 3.11 ± 2.78 | 3.89 ± 2.92 | 3.67 ± 4.10 | 2.22 ± 2.32 |
|  | HR | −47.67 ± 8.88[c] | −38.89 ± 9.47[b] | −23.67 ± 10.01 | −11.89 ± 8.73 | −2.67 ± 4.14 |

TABLE 6-continued

Heart Rate and Blood Pressure Changes of Rats Induced by Guaiacoxypropanolamines

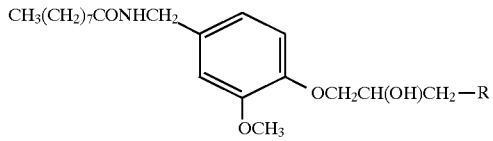

change in BP (mmHg) or HR (beats/min) at the following times after dosing[a]

| R | | 5 min | 10 min | 15 min | 30 min | 60 min |
|---|---|---|---|---|---|---|
| NH-n-$C_3H_7$ | BP | −1.78 ± 1.71 | −2.56 ± 1.47 | −3.11 ± 1.81 | −2.44 ± 1.66 | −0.56 ± 0.50 |
| | HR | −42.56 ± 7.65[c] | −35.33 ± 6.05[c] | −32.00 ± 5.25[c] | −14.11 ± 5.16 | −6.89 ± 4.32 |
| NH-i-$C_3H_7$ | BP | −0.44 ± 2.05 | −1.22 ± 2.29 | −2.89 ± 2.03 | −6.67 ± 2.51 | −1.33 ± 0.98 |
| | HR | −50.22 ± 7.29[c] | −40.78 ± 7.64[c] | −35.44 ± 7.32[c] | −32.67 ± 9.24[b] | −20.00 ± 6.15[b] |
| NH-n-$C_4H_9$ | BP | −0.22 ± 1.74 | −1.22 ± 1.59 | −1.22 ± 1.77 | 0.11 ± 1.54 | 3.33 ± 2.82 |
| | HR | −40.00 ± 3.74[c] | −33.78 ± 5.08[c] | −26.22 ± 6.56[b] | −15.33 ± 5.24 | −3.67 ± 2.55 |
| NH-i-$C_4H_9$ | BP | −2.75 ± 2.29 | 1.63 ± 2.07 | 1.63 ± 1.71 | 2.00 ± 1.86 | 0.25 ± 1.91 |
| | HR | −39.88 ± 8.60[c] | −35.25 ± 7.98[b] | −27.13 ± 7.76 | 4.13 ± 8.20 | 3.13 ± 7.90 |
| NH-s-$C_4H_9$ | BP | 4.11 ± 2.76 | 4.89 ± 3.37 | 3.33 ± 3.74 | −0.88 ± 3.11 | 1.22 ± 1.47 |
| | HR | −38.56 ± 11.30[b] | −35.44 ± 12.46 | −32.33 ± 11.96 | −25.11 ± 9.49 | −9.56 ± 7.03 |
| NH-t-$C_4H_9$ | BP | 3.13 ± 5.66 | 3.38 ± 5.08 | 2.38 ± 5.41 | 1.25 ± 5.45 | 4.63 ± 3.51 |
| | HR | −45.00 ± 4.20[c] | −37.75 ± 4.44[c] | −29.50 ± 5.31[c] | −24.88 ± 8.47[b] | −18.50 ± 5.13[b] |
| NH-n-$C_5H_{11}$ | BP | −4.67 ± 1.71 | −1.67 ± 1.87 | −0.88 ± 3.00 | 3.67 ± 2.66 | 2.44 ± 1.96 |
| | HR | −25.11 ± 5.81[c] | −23.33 ± 2.41[c] | −10.22 ± 2.38[c] | −5.78 ± 7.89 | −6.56 ± 4.38 |
| $NHC_5H_{11}$ | BP | −2.78 ± 2.33 | −2.56 ± 1.42 | −3.22 ± 1.78 | −1.33 ± 1.38 | 0.67 ± 0.47 |
| | HR | −28.11 ± 9.34[b] | −28.89 ± 6.30[c] | −22.78 ± 5.04[c] | −2.22 ± 7.28 | −3.33 ± 5.69 |
| NH-n-$C_6H_{13}$ | BP | −2.22 ± 1.42 | −2.89 ± 1.61 | −4.44 ± 2.93 | −2.11 ± 2.77 | 1.89 ± 1.13 |
| | HR | −35.56 ± 8.71[b] | −24.11 ± 3.31[c] | −14.89 ± 7.10 | −12.67 ± 6.59 | −8.00 ± 5.64 |
| NH-c-$C_6H_{11}$ | BP | −4.11 ± 2.89 | −4.22 ± 2.29 | −3.67 ± 2.39 | 1.33 ± 2.69 | 0.67 ± 2.45 |
| | HR | −32.33 ± 15.44 | −28.44 ± 16.54 | −11.67 ± 9.26 | −1.78 ± 8.96 | 2.78 ± 9.64 |
| propranolol | BP | −2.83 ± 1.81 | −6.33 ± 2.16 | −6.50 ± 3.26 | −4.67 ± 2.66 | 2.17 ± 3.29 |
| | HR | −57.28 ± 5.94[c] | −63.85 ± 7.18[c] | −65.28 ± 8.43[c] | −62.57 ± 9.06[c] | −52.14 ± 10.93[c] |
| saline | BP | 2.52 ± 1.51 | 1.42 ± 1.00 | 0.72 ± 0.54 | 0.52 ± 0.43 | 0.41 ± 0.41 |
| | HR | 1.72 ± 1.01 | 1.01 ± 0.82 | 1.01 ± 0.71 | 0.53 ± 0.32 | 0.32 ± 0.33 |

[a]Data were expressed as means ± SE (n = 8). Administered iv at a dose of 1.0 mg ± kg.
[b]$p < 0.05$ as compared to saline.
[c]$p < 0.001$ as compared to saline.

TABLE 7 pA$_2$ Values of Guaiacoxypropanolamines on Isolated Guinea Pig Atria $CH_3(CH_2)_7CONHCH_2$—[ring with $OCH_3$]—$OCH_2CH(OH)CH_2$—R atria (PR[a])

| R | positive chronotropic | positive inotropic |
|---|---|---|
| propranolol | 8.12 ± 0.06 (1.00) | 8.42 ± 0.09 (1.00) |
| $NHCH_3$ | 6.53 ± 0.12 (0.03) | 7.13 ± 0.02 (0.05) |
| $NHC_2H_5$ | 6.93 ± 0.09 (0.07) | 7.27 ± 0.09 (0.07) |
| $NHC_3H_5$ | 7.03 ± 0.05 (0.08) | 7.60 ± 0.08 (0.15) |
| NH-n-$C_3H_7$ | 6.79 ± 0.01 (0.05) | 7.75 ± 0.07 (0.21) |
| NH-i-$C_3H_7$ | 7.77 ± 0.08 (0.45) | 8.07 ± 0.06 (0.45) |
| NH-n-$C_4H_9$ | 7.23 ± 0.07 (0.13) | 7.27 ± 0.07 (0.07) |
| NH-i-$C_4H_9$ | 6.93 ± 0.06 (0.06) | 7.57 ± 0.11 (0.14) |
| NH-s-$C_4H_9$ | 6.92 ± 0.10 (0.07) | 7.65 ± 0.09 (0.17) |
| NH-t-butyl | 7.40 ± 0.09 (0.19) | 7.80 ± 0.07 (0.24) |
| NH-n-$C_5H_{11}$ | 7.19 ± 0.02 (0.12) | 7.55 ± 0.04 (0.14) |
| $NHC_5H_{11}$ | 7.25 ± 0.10 (0.14) | 7.26 ± 0.08 (0.07) |
| NH-n-$C_6H_{13}$ | 6.03 ± 0.02 (0.01) | 7.18 ± 0.06 (0.06) |

[a]Potency ratio (PR) = Antilog (pA$_2$ antagonist − pA$_2$ propranolol) with respect to propranolol.

Figure 19A:
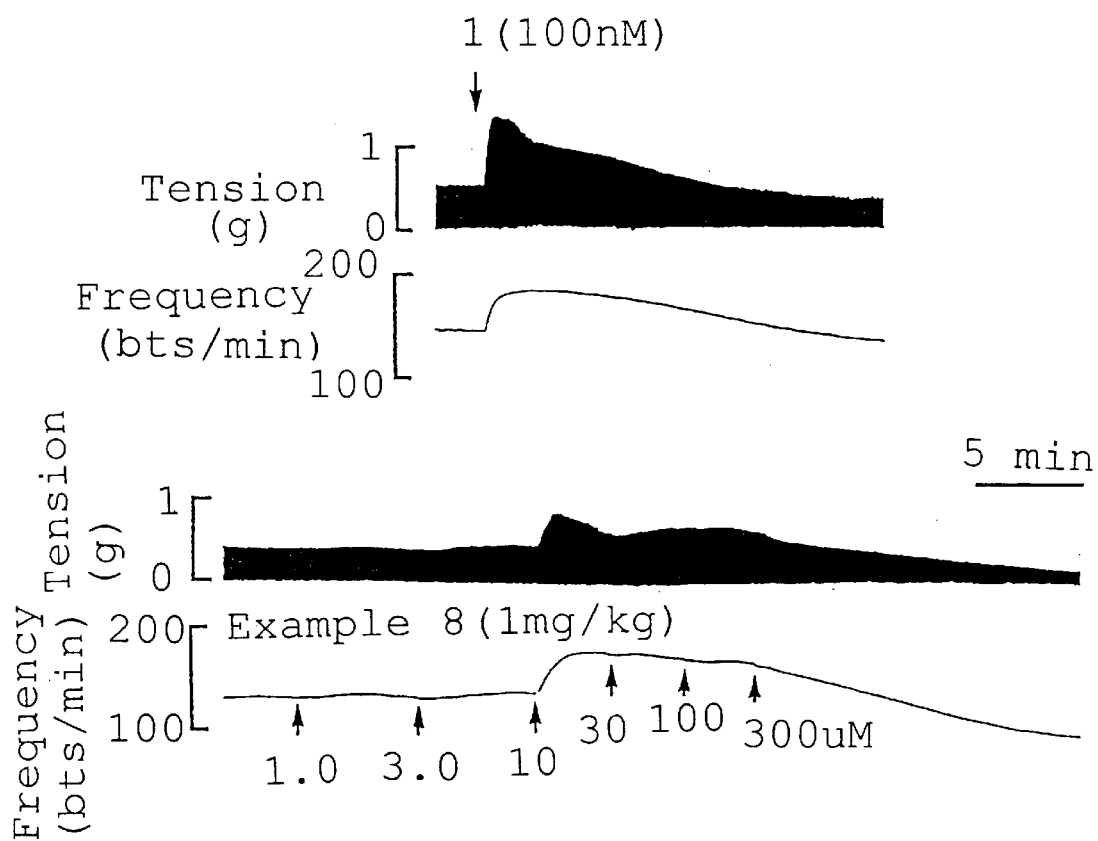
Figure 19B:
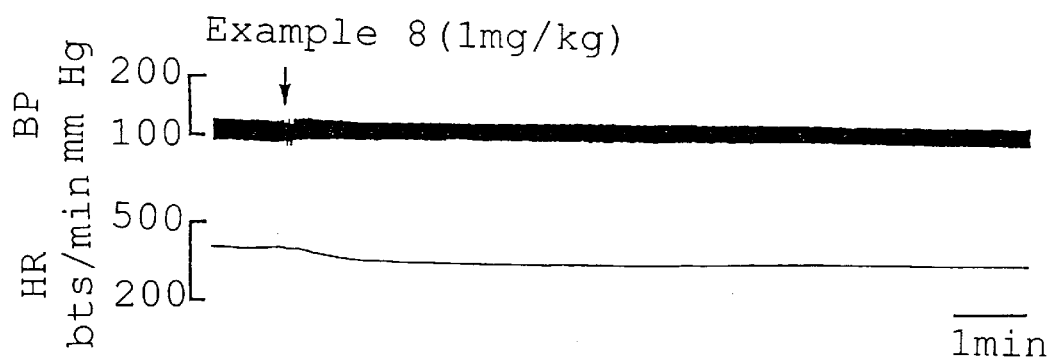
Figure 20:
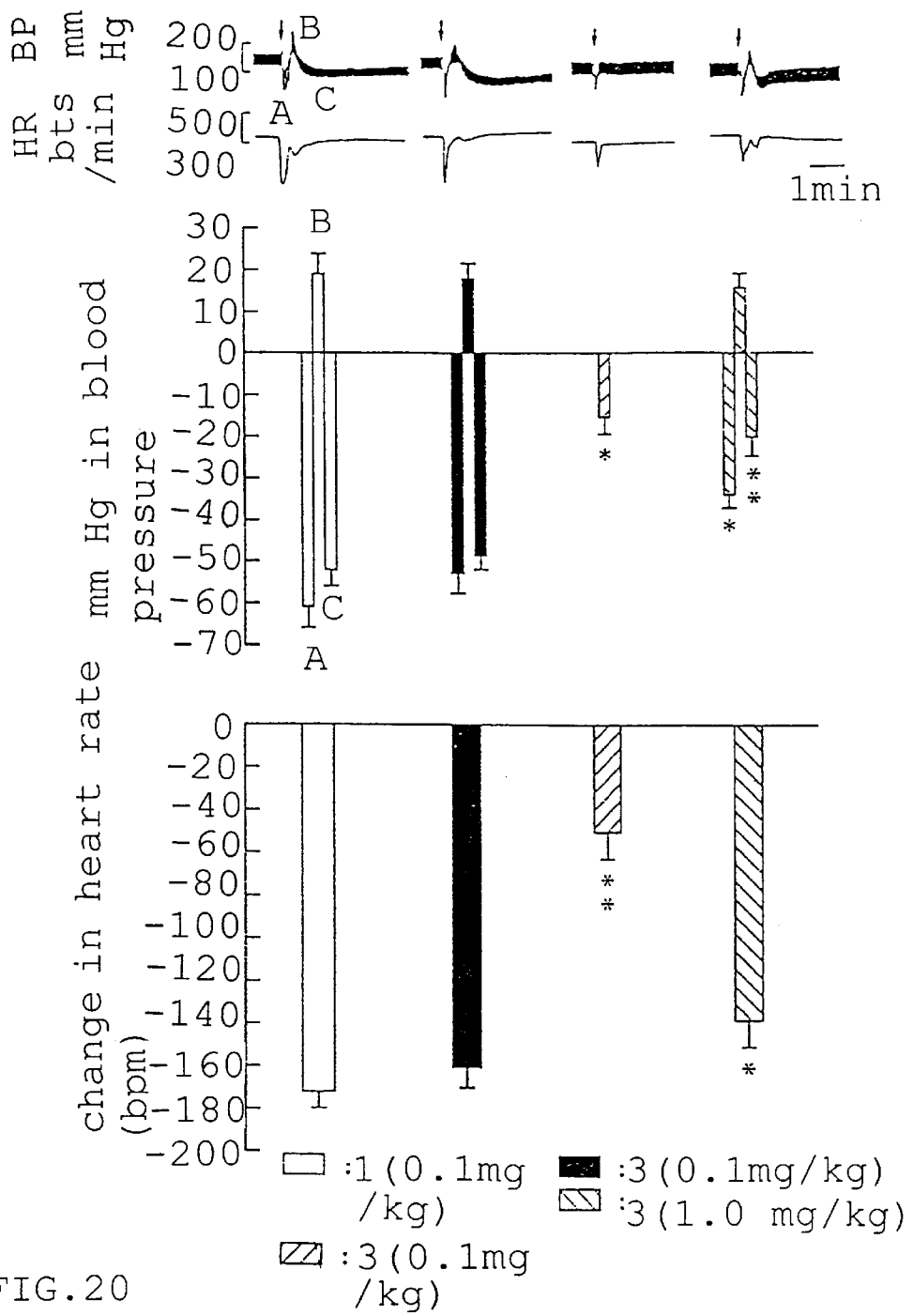

With respect to Examples 7–27 all the cardiovascular pharmacological results are shown in Table 6, Table 7, FIG. 19(A), FIG. 19(B) and FIG. 20. All these compounds exhibit a bradycardia effect and beta adrenergic blocking activity. For comparison, the PA2 value of these compounds are listed in Table 7. Some analogs with a 3-methoxy, 4-hydroxy benzyl or phenyl structure, such as eugenol, isoeugenol, vanillin, ethyl vanillic acid ester, ferulic acid can be used as the starting material to synthesize beta blockers by reaction with isopropylamine and propanolamine.

What is claimed is:

1. A compound which is a member selected from the group consisting of
N-[4-o-(2,3-epoxypropoxy)-3-methoxybenzyl]-nonamide, NVAE).
N-[4-(2-hydroxy-3-(isopropylamino)propoxy)-3-methoxybenzyl]-nonamide,NVAEN)
N-[4-(2-hydroxy-3-(n-propylamino)propoxy)-3-methoxybenzyl]-nonamide
N-[4-)-(2-hydroxy-3-(methylamino)propoxy)-3-methoxybenzyl]-nonamide
N-[4-(2-hydroxy-3(ethylamino)propoxy)-3-methoxybenzyl]-nonamide
N-[4-o-(2-hydroxy-3-(allylamino)propoxy)-3-methoxybenzyl]-nonamide
N-[4-(2-hydroxy-3-(cyclopropylamino)propoxy)-3-methoxybenzyl]-nonamide
N-[4-(2-hydroxy-3-((n-butylamino)propoxy)-3-methoxybenzyl]-nonamide
N-[4-(2-hydroxy-3-(iso-butylamino)propoxy)-3-methoxybenzyl]-nonamide N-[4-(2-hydroxy-3-(sec-butylamino)propoxy)-3-methoxybenzyl]-nonamide
N-[4-(2-hydroxy-3-(tert-butylamino)propoxy)-3-methoxybenzyl]-nonamide
N-[4-(2-hydroxy-3-(n-pentylamino)propoxy)-3-methoxybenzyl]-nonamide
N-[4-(2-hydroxy-3-(3-aminopentylamino)propoxy)-3-methoxybenzyl]-nonamide
N-[4-(2-hydroxy-3-(n-hexylamino)propoxy)-3-methoxybenzyl]-nonamide
N-[4-(2-hydroxy-3-(cyclohexylamino)propoxy)-3-methoxybenzyl]-nonamide
N-[4-(2-hydroxy-3-(n-heptylamino)propoxy)-3-methoxybenzyl]-nonamide
N-[4-(2-hydroxy-3-(benzylamino)propoxy)-3-methoxybenzyl]nonamide
N-(4-o-dimethylaminoethyl-3-methoxybenzyl)-nonamide
N-(4-o-diethylaminoethyl-3-methoxybenzyl)-nonamide
N-(4-o-pyridylmethyl-3-methoxybenzyl)-nonamide and
N-(4-o-piperidylethyl-3-methoxybenzyl)-nonamide.

2. A method of treatment of a living subject in need of a B-adrenergic blocker to reduce the blood pressure which consists of administering to said subject a composition containing an effective amount of a compound which is a member selected from the group consisting of
N-[4-o-(2,3-epoxypropoxy)-3-methoxybenzyl]-nonamide, NVAE)
N-[4-(2-hydroxy-3-(isopropylamino)propoxy)-3-methoxybenzyl]-nonamide,NVAEN)
N-[4-(2-hydroxy-3-(n-propylamino)propoxy)-3-methoxybenzyl]-nonamide
N-[4)-(2-hydroxy-3-(methylamino)propoxy)-3-methoxybenzyl]-nonamide
N-[4-(2-hydroxy-3(ethylamino)propoxy)-3-methoxybenzyl]-nonamide
N-[4-o-(2-hydroxy-3-(allylamino)propoxy)-3-methoxybenzyl]-nonamide
N-[4-(2-hydroxy-3-(cyclopropylamino)propoxy)-3-methoxybenzyl]-nonamide
N-[4-(2-hydroxy-3-((n-butylamino)propoxy)-3-methoxybenzyl]-nonamide
N-[4-(2-hydroxy-3-(iso-butylamino)propoxy)-3-methoxybenzyl]-nonamide
N-[4-(2-hydroxy-3-(sec-butylamino)propoxy)-3-methoxybenzyl]-nonamide
N-[4-(2-hydroxy-3-(tert-butylamino)propoxy)-3-methoxybenzyl]-nonamide
N-[4-(2-hydroxy-3-(n-pentylamino)propoxy)-3-methoxybenzyl]-nonamide
N-[4-(2-hydroxy-3-(3-aminopentylamino)propoxy)-3-methoxybenzyl]-nonamide
N-[4-(2-hydroxy-3-(n-hexylamino)propoxy)-3-methoxybenzyl]-nonamide
N-[4-(2-hydroxy-3-(cyclohexylamino)propoxy)-3-methoxybenzyl]-nonamide
N-[4-(2-hydroxy-3-(n-heptylamino)propoxy)-3-methoxybenzyl]-nonamide
N-[4-(2-hydroxy-3-(benzylamino)propoxy)-3-methoxybenzyl]nonamide
N-(4-o-dimethylaminoethyl-3-methoxybenzyl)-nonamide
N-(4-o-diethylaminoethyl-3-methoxybenzyl)-nonamide
N-(4-o-pyridylmethyl-3-methoxybenzyl)-nonamide and
N-(4-o-piperidylethyl-3-methoxybenzyl)-nonamide.

3. A β adrenegic blocker composition in unit dosage form containing a compound according to claim 1 in the amount of 60 mgs per dose and a therapeutically inert carrier.

* * * * *